United States Patent
Fukuda et al.

(10) Patent No.: US 7,790,114 B2
(45) Date of Patent: Sep. 7, 2010

(54) REAGENT-CONTAINING ASSEMBLY

(75) Inventors: Kazuya Fukuda, Kobe (JP); Toshikatsu Fukuju, Akashi (JP); Kazunori Mototsu, Kobe (JP); Motoki Koyama, Kobe (JP); Toshihiro Ootani, Kobe (JP)

(73) Assignee: Sysmex Corporation, Kobe (JP)

( * ) Notice: Subject to any disclaimer, the term of this patent is extended or adjusted under 35 U.S.C. 154(b) by 290 days.

(21) Appl. No.: 11/973,718

(22) Filed: Oct. 9, 2007

(65) Prior Publication Data

US 2008/0085222 A1 Apr. 10, 2008

(30) Foreign Application Priority Data

Oct. 10, 2006 (JP) ............................. 2006-276464

(51) Int. Cl.
*B01L 3/00* (2006.01)
*B01L 9/00* (2006.01)

(52) U.S. Cl. .................... 422/99; 422/102; 422/104

(58) Field of Classification Search .................. 422/102
See application file for complete search history.

(56) References Cited

U.S. PATENT DOCUMENTS

| | | | |
|---|---|---|---|
| 5,885,530 A * | 3/1999 | Babson et al. ................. 422/65 |
| 6,193,933 B1 * | 2/2001 | Sasaki et al. .................. 422/64 |
| 6,511,634 B1 | 1/2003 | Bradshaw et al. | |
| 6,866,820 B1 | 3/2005 | Otto et al. | |
| 2006/0120922 A1 * | 6/2006 | Matsumoto ................. 422/64 |

FOREIGN PATENT DOCUMENTS

| EP | 1 273 920 A2 | 1/2003 |
|---|---|---|
| EP | 1273920 A2 * | 1/2003 |
| EP | 1 647 826 A1 | 4/2006 |
| GB | 1 306 014 | 2/1973 |
| JP | 2004-177254 | 6/2004 |
| JP | 2004177254 A * | 6/2004 |
| WO | WO 95/01919 | 1/1995 |
| WO | WO 98/00697 | 1/1998 |

OTHER PUBLICATIONS

European Search Report for Corresponding European Patent Application No. 07019707.4 dated Mar. 12, 2008.

* cited by examiner

*Primary Examiner*—Jill Warden
*Assistant Examiner*—Jennifer Wecker
(74) *Attorney, Agent, or Firm*—Brinks Hofer Gilson & Lione

(57) ABSTRACT

A reagent-containing assembly comprising: a reagent-accommodating section comprising an opening sealed by a seal member; and a seal-opening section comprising a breaking portion for breaking the seal member, and a suction hole configured to provide access to the reagent-accommodating section; wherein the reagent-accommodating section and the seal-opening section are configured for detachable engagement with each other is disclosed.

18 Claims, 37 Drawing Sheets

REAGENT-CONTAINING ASSEMBLY

RELATED APPLICATIONS

This application claims priority under 35 U.S.C. §119 to Japanese Patent Application No. 2006-276464 filed Oct. 10, 2006, the entire content of which is hereby incorporated by reference.

FIELD OF THE INVENTION

The present invention relates to reagent-containing assemblies, in particular, to a reagent-containing assembly having an opening sealed by a seal member.

BACKGROUND

Conventionally, a reagent-containing assembly having an opening sealed with reagent accommodated therein is known (see e.g., Japanese Laid-Open Patent Publication No. 2004-177254).

The reagent-containing assembly disclosed in Japanese Laid-Open Patent Publication No. 2004-177254 includes a reagent container for accommodating reagent, and a cap to be attached to the reagent container. The cap includes a circular disc shaped sealing body, arranged in the vicinity of the opening of the reagent container, made up of an elastic body radially formed with slits from a center towards the outer periphery, and an openable/closable member that moves downward by being pushed from above thereby pushing and widening the slit of the sealing body downward and opening the slit. The openable/closable member is biased upward by a spring member.

In the reagent-containing assembly disclosed in Japanese Laid-Open Patent Publication No. 2004-177254, the slit of the sealing body is opened by pushing the openable/closable member from above thereby enabling division of reagents when dividing the reagents. After dividing the reagent, the pushing on the openable/closable member is released, and the openable/closable member moves upward by the biasing force of the spring member, whereby the shape of the slit that was pushed and widened of the sealing body made of elastic body restores. The opening of the reagent container thereby closes.

However, since the reagent-containing assembly of Japanese Laid-Open Patent Publication No. 2004-177254 is configured such that the reagent container closes when the shape of the slit of the sealing body that was pushed and widened restores by elastic force, the reagent container cannot be sealed. Thus, the opening of the reagent container is sealed with a sealing dedicated cap when supplying the reagent to the user, and the user must remove such sealing dedicated cap of the reagent container when using the reagent (when suctioning the reagent) and changing such cap with the cap described above. The reagent accommodated in the reagent container might get contaminated, or the reagent might attach to the user when changing the cap, thereby causing contamination accidents.

SUMMARY OF THE INVENTION

The scope of the present invention is defined solely by the appended claims, and is not affected to any degree by the statements within this summary.

A first aspect of the present invention is a reagent-containing assembly comprising: a reagent-accommodating section comprising an opening sealed by a seal member; and a seal-opening section comprising a breaking portion for breaking the seal member, and a suction hole configured to provide access to the reagent-accommodating section; wherein the reagent-accommodating section and the seal-opening section are configured for detachable engagement with each other.

A second aspect of the present invention is a reagent-containing assembly comprising: a reagent container comprising an opening sealed by a seal member; a holder configured for holding the reagent container; and a case, movable in a direction towards a bottom part of the holder, configured for covering the reagent container; wherein the case comprises a breaking portion for breaking the seal member, and a suction hole configured to provide access to the reagent container; and the holder and the case are configured for detachable engagement with each other.

A third aspect of the present invention is a reagent-containing assembly comprising: a holder for holding a reagent container comprising an opening sealed by a seal member; and a case, movable in a direction towards a bottom part of the holder, configured for covering the reagent container; wherein the case comprises a breaking portion for breaking the seal member, and a suction hole to provide access to the reagent container; and the holder and the case are configured for detachable engagement with each other.

DETAILED DESCRIPTION OF THE PREFERRED EMBODIMENTS

The preferred embodiments of the present invention are described hereinafter with reference to the drawings.

Figure 1:
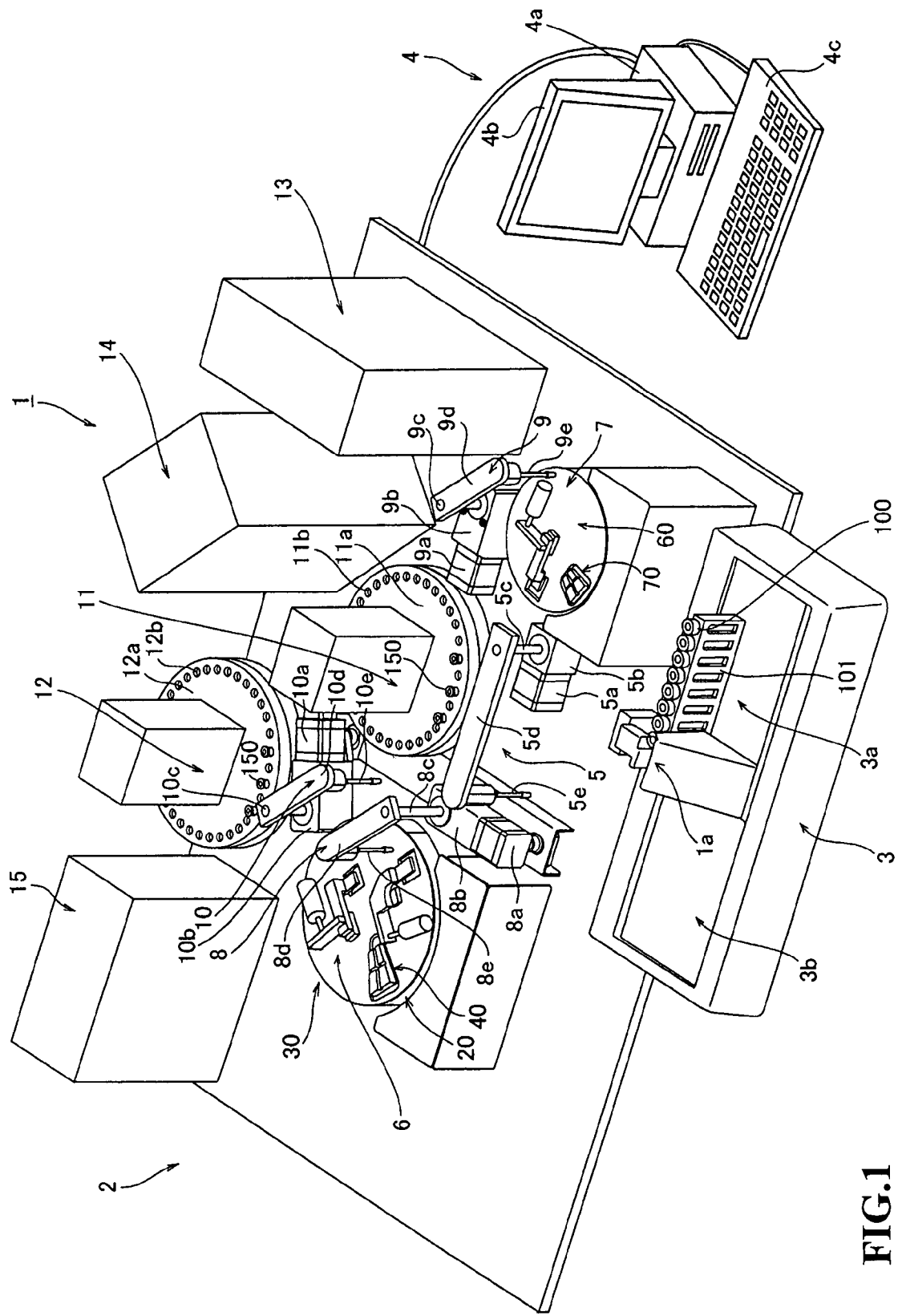
FIG. 1 is a perspective view showing an overall configuration of an immune analyzer using a reagent-containing assembly according to one embodiment of the present invention.
Figure 2:
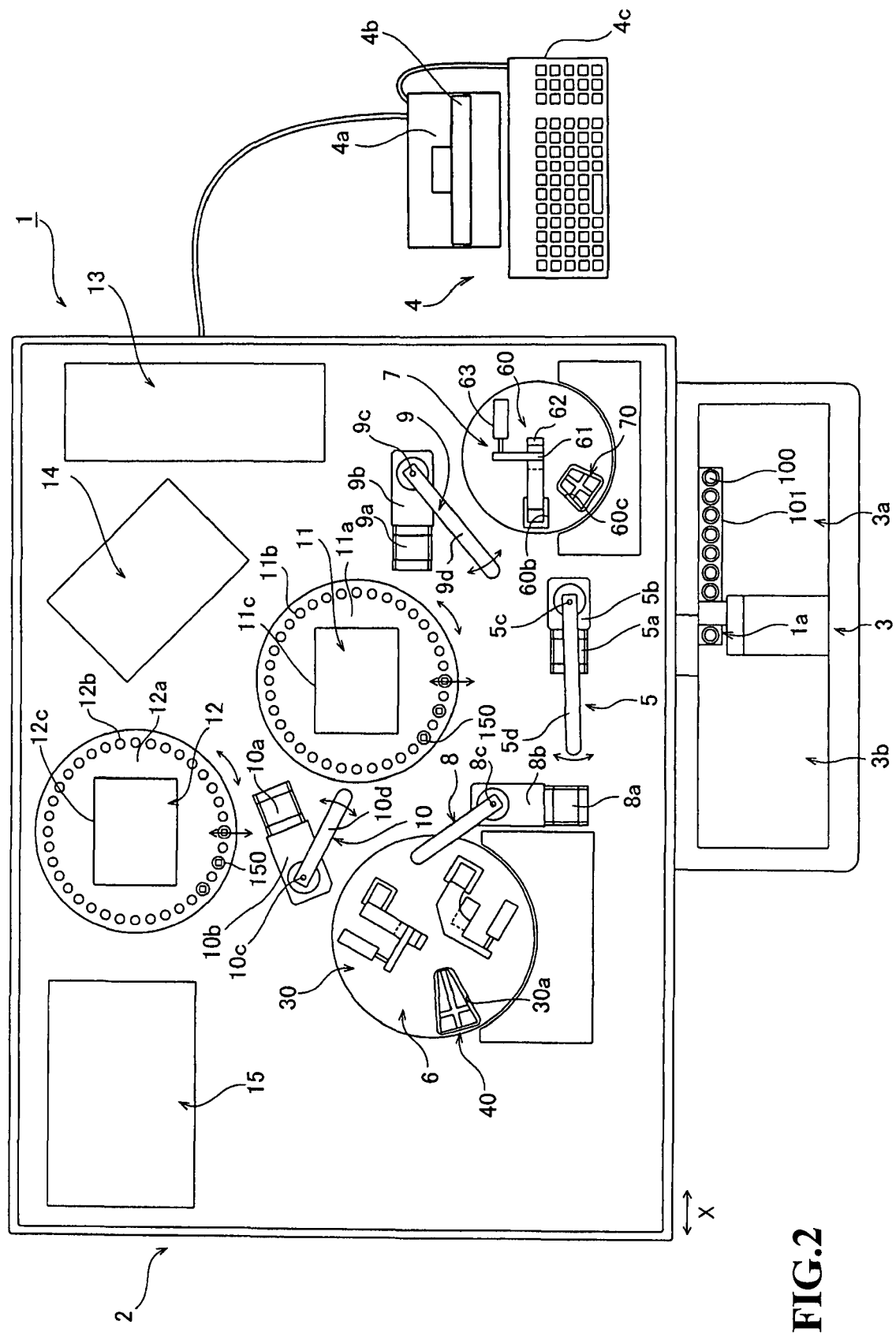
FIG. 2 is a plan view of the immune analyzer shown in FIG. 1.

FIGS. 1 and 2 are perspective view and plan view, respectively, showing an overall configuration of an immune analyzer using a reagent-containing assembly according to one embodiment of the present invention. FIGS. 3 to 6 and FIG. 20 are views describing details of each unit of the immune analyzer according to the one embodiment shown in FIG. 1. The overall configuration of the immune analyzer 1 according to one embodiment of the present invention will now be described with reference to FIGS. 1 to 6, and FIG. 20.

The immune analyzer 1 according to one embodiment of the present invention is an apparatus for carrying out examinations on various items such as hepatitis B, hepatitis C, tumor marker, and thyroid hormone using samples such as blood. In the immune analyzer 1, magnetic particles (R2 reagent) are bonded to a trapped antibody (R1 reagent) bonded to an antigen contained in a sample such as blood, which is the measuring object, and thereafter, the bound antigen, trapped antibody, and magnetic particles are attracted to a magnet (not shown) of a BF (Bound Free) separator 14 (see FIGS. 1 and 2) to remove the R1 reagent containing non-reactive (free) trapped body. A labeled antibody (R3 reagent) is bonded to the antigen bound with magnetic particles, and thereafter, the bound magnetic particles, antigen, and labeled antibody are attracted to a magnet of a BF separator 14 to remove a R3 reagent containing non-reactive (free) labeled antibody. Furthermore, a light emitting substrate (R5 reagent) that emits light in the reaction process with the labeled antibody is added, and a light emitting amount generated through the reaction of the labeled antibody and the light emitting substrate is measured. After such processes, the antigen contained in the sample that bonds with the labeled antibody is quantitatively measured.

Figure 3:
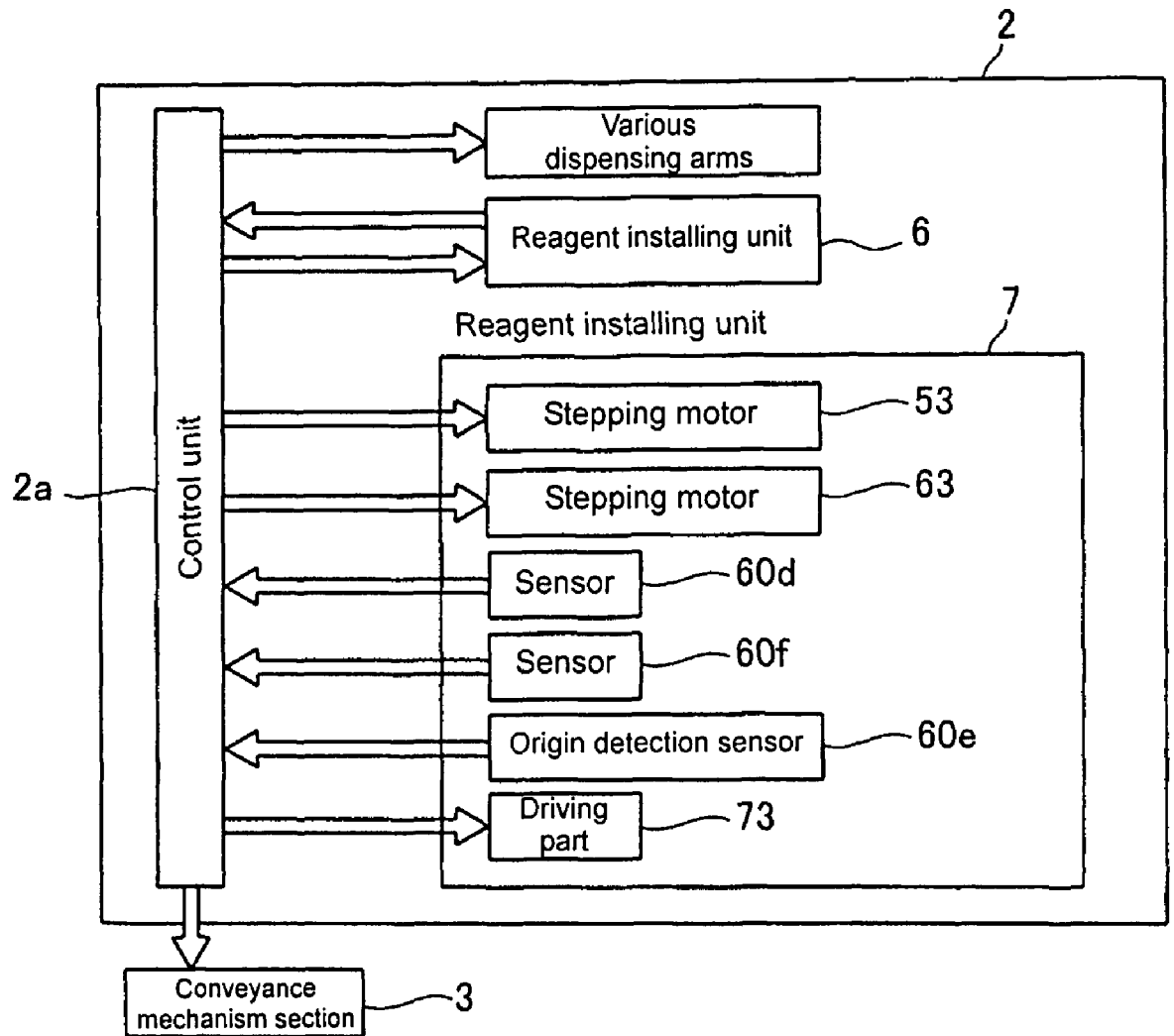
FIG. 3 is a block diagram including a control unit of a measurement mechanism section of the immune analyzer using the reagent-containing assembly according to the one embodiment of the present invention.
Figure 4:
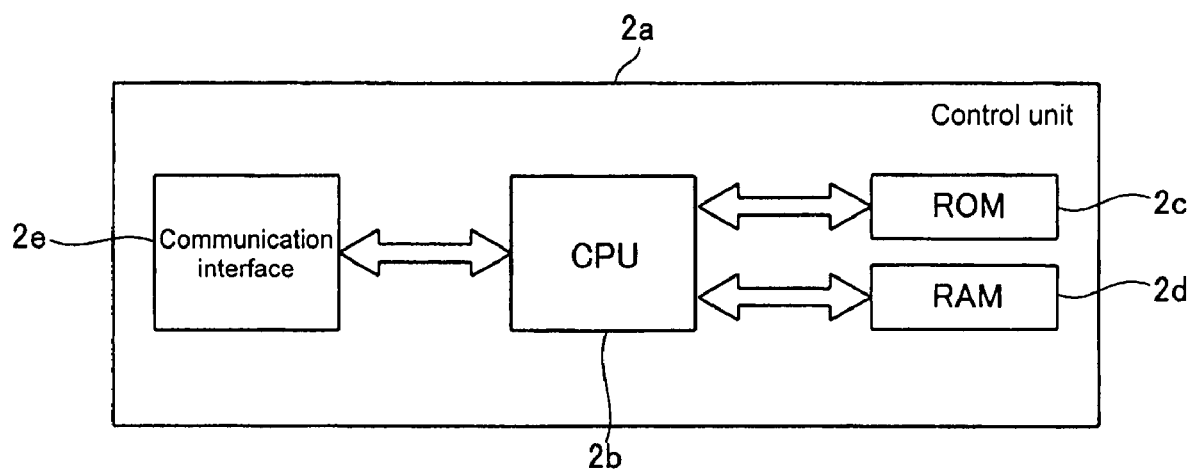
FIG. 4 is a block diagram showing a configuration of the control unit of the measurement mechanism section shown in FIG. 3.

As shown in FIGS. 1 and 2, the immune analyzer 1 includes a measurement mechanism section 2, a sample conveyance section (sampler) 3 arranged on the front surface side of the measurement mechanism section 2, and a control device 4 including PC (personal computer) electrically connected to the measurement mechanism section 2. The measurement mechanism section 2 is configured by a sample dispensing arm 5, reagent installing units 6 and 7, reagent dispensing arms 8, 9, and 10, a primary reaction unit 11 and a secondary reaction unit 12, a cuvette supplying unit 13, a BF separator 14, and a detector 15. As shown in FIG. 3, each mechanism (various dispensing arms, reagent installing unit 6, and reagent installing unit 7, and the like) in the measurement mechanism section 2 are controlled by a control unit 2a arranged in the measurement mechanism section 2. Specifically, the control unit 2a receives signals of various sensors (sensors 60d, 60f and origin detection sensor 60e, and the like) arranged in the reagent installing unit 7, and controls the drive of various driving sources (stepping motors 53, 63, and motor 73, and the like) arranged in the reagent installing unit 7. The conveyance mechanism section 3 is also controlled by the control unit 2a. The various dispensing arms, various sensors, and various driving sources will be described in detail below.

The control unit 2a is mainly configured by a CPU 2b, a ROM 2c, a RAM 2d, and a communication interface 2e.

The CPU 2b executes computer programs stored in the ROM 2c and the computer programs read by the RAM 2d. The ROM 2c stores computer programs executed by the CPU 2b, data used in executing the computer program, and the like. The RAM 2d is used to read out the computer program stored in the ROM 2c. In executing the computer program, the RAM 2d is used as a work region of the CPU 2b.

The communication interface 2e is connected to the control device 4, and transmits optical information (data of received light amount generated by reaction of the labeled antibody and light emitting substrate) of the sample to the control device 4, and receives signals from the control unit 4a of the control device 4. The communication interface 2e has a function of transmitting a command from the CPU 2b for driving each unit of the conveyance mechanism section 3 and the measurement mechanism section 2.

As shown in FIGS. 1 and 2, the sample conveyance section 3 is configured to convey a rack 101 mounted with a plurality of test tubes 100 accommodating the sample to a position corresponding to a suction position 1a at where the sample dispensing arm 5 suctions the sample. The sample conveyance section 3 includes a rack set part 3a for setting the rack 101 in which the test tubes 100 accommodating non-processed sample are mounted, and a rack storing part 3b for storing the rack 101 in which the test tubes 100 accommodating the dispensing processed sample are mounted. The test tube 100 accommodating the non-processed sample is conveyed to a position corresponding to the suction position 1a of the sample dispensing arm 5, so that the sample dispensing arm 5 suctions the sample such as blood in the test tube 100, and thereafter, the rack 101 mounted with the test tube 100 is stored in the rack storing part 3b.

The control device 4 (FIG. 1) consists of a personal computer (PC), and includes a control unit 4a including CPU, ROM, RAM, a display unit 4b and a keyboard 4c. The display unit 4b is arranged to display result of analysis obtained by analyzing data of digital signals transmitted from a detector 15.

Figure 5:
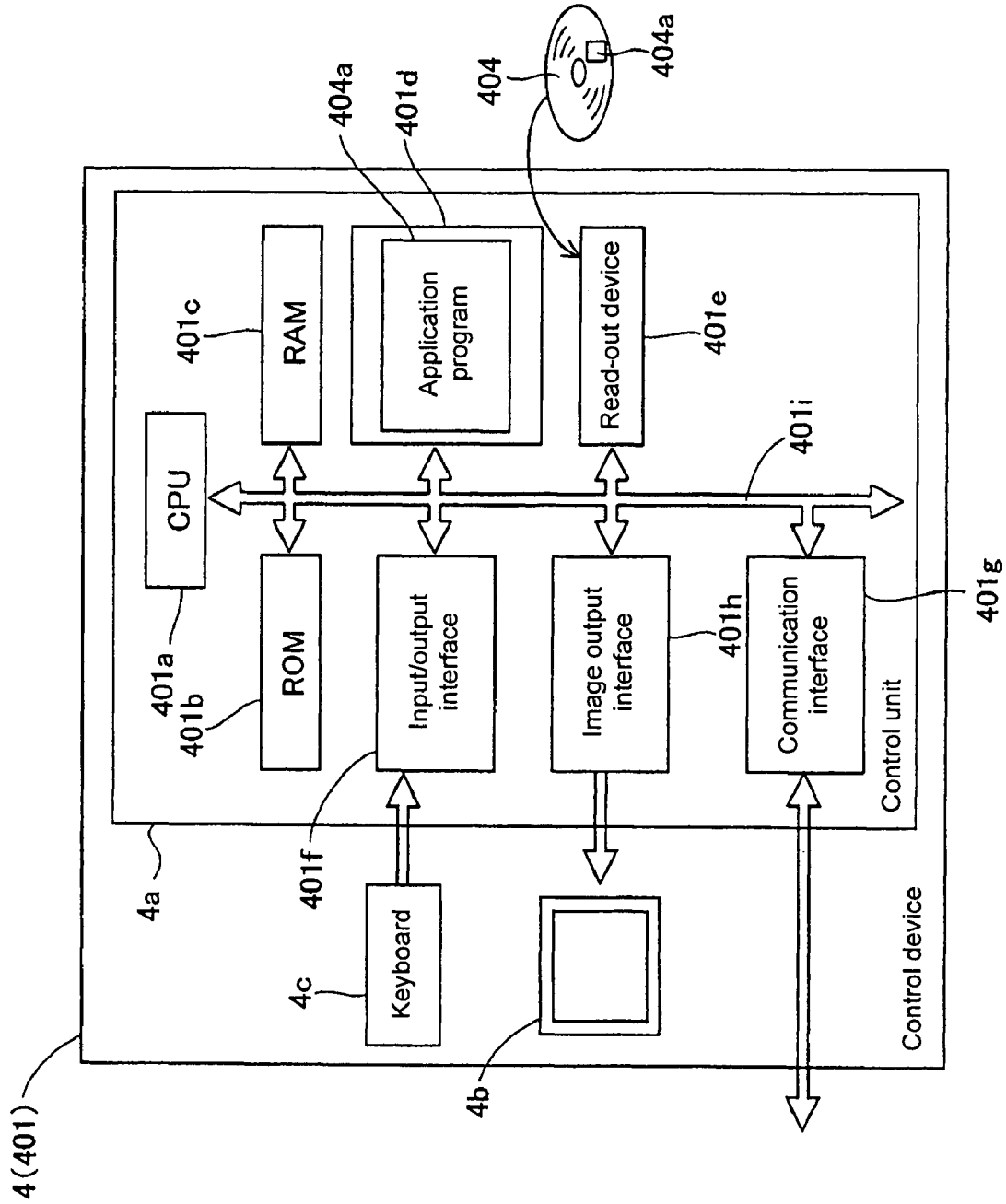
FIG. 5 is a block diagram showing a control device of the immune analyzer using the reagent-containing assembly according to the one embodiment of the present invention.

The configuration of the control device 4 will now be described. As shown in FIG. 5, the control device 4 is configured by a computer 401 mainly consisting of the control unit 4a, the display unit 4b, and the keyboard 4c. The control unit 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a executes computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The immune analysis application program 404a according to the present embodiment is also installed in the hard disc 401d.

The read-out device 401e is configured by flexible disc drive, CD-ROM drive, DVD-ROM drive, and the like, and is able to read out computer programs and data recorded on a portable recording medium 404. The immune analysis application program 404a is stored in the portable recording medium 404, where the computer 401 reads out the application program 404a from the portable recording medium 404, and installs the application program 404a to the hard disc 401d.

The application program 404a is not only provided by the portable recording medium 404, but also provided through communication line (wired or wireless) from external devices communicatably connected with the computer 401 through the communication line. For instance, the application program 404a may be stored in the hard disc of the server computer on the Internet, so that the computer 401 can access the server computer to download the application program 404a and install the application program 404a to the hard disc 401d.

Operating system providing graphical user interface environment such as Windows® manufactured and sold by US Microsoft Co. is installed in the hard disc 401d. In the following description, the application program 404a according to the first embodiment is assumed to operate on the operating system.

The output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet® interface. The computer 401 transmits and receives data with the measurement mechanism section 2 using a predetermined communication protocol by means of the communication interface 401g.

The image output interface 401h is connected to the display unit 4b configured by LCD, CRT, or the like, and is configured to output an image signal corresponding to the image data provided from the CPU 401a to the display unit 4b. The display unit 4b displays the image (screen) according to the input image signal.

The immune analysis application program 404a installed in the hard disc 401d of the control unit 4a measures the amount of antigen in the measurement specimen using the received light amount (data of digital signal) of the measurement specimen transmitted from the detector 15 of the measurement mechanism section 2.

The sample dispensing arm 5 (see FIGS. 1 and 2) has a function of dispensing the sample in the test tube 100 conveyed to the suction position 1a by the sample conveyance section 3 into a cuvette 150 held by a holder 11b of a rotatable table 11a of the primary reaction unit 11 to be hereinafter described. As shown in FIGS. 1 and 2, the sample dispensing arm 5 includes a motor 5a, a drive transmitting part 5b connected to the motor 5a, and an arm 5d attached to the drive transmitting part 5b by way of a shaft 5c. The drive transmitting part 5b is configured to turn the arm 5d with the shaft 5c as the center by the driving force from the motor 5a, and move the arm in the up and down direction (Z direction). A pipette 5e for suctioning and discharging the sample is arranged at the distal end of the arm 5d.

The reagent installing unit 6 (see FIGS. 1 and 2) is provided to install a reagent-containing assembly 200 (see FIG. 20) for holding a reagent container in which R1 reagent containing trapped antibody is accommodated and a reagent container in which R3 reagent containing labeled antibody is accommodated. As shown in FIG. 1, the reagent installing unit 6 includes a reagent holder 20 for holding the reagent-containing assembly 200, a lid 30 attached to the reagent holder 20, and a raising and lowering unit 40 for replacing the reagent-containing assembly 200 in the reagent holder 20 through a hole 30a formed in the lid 30.

The reagent installing unit 7 (see FIGS. 1 and 2) is arranged to install a reagent-containing assembly 300 (see FIG. 22) for holding a test container in which a R2 reagent containing magnetic particles is accommodated. The configuration of the reagent installing unit 7 will be hereinafter described in detail.

The reagent dispensing arm 8 (see FIGS. 1 and 2) has a function of suctioning the R1 reagent in the reagent-containing assembly installed in the reagent installing unit 6 and dispensing the suctioned R1 reagent into the cuvette 150 dispensed with the sample of the primary reaction unit 11. The reagent dispensing arm 8 includes a motor 8a, a drive transmitting part 8b connected to the motor 8a, and an arm 8d attached to the drive transmitting part 8b by way of a shaft 8c. The drive transmitting part 8b is configured to turn the arm 8d with the shaft 8c as the center by the driving force from the motor 8a, and move the arm in the up and down direction. A pipette 8e (see FIG. 1) for suctioning and discharging the R1 reagent in the reagent-containing assembly is arranged at the distal end of the arm 8d. That is, the pipette 8e is configured to suction the R1 reagent in the reagent-containing assembly installed in the reagent installing unit 6, and thereafter, dispense the suctioned R1 reagent into the cuvette 150 dispensed with the sample of the primary reaction unit 11.

The reagent dispensing arm 9 (see FIGS. 1 and 2) has a function of dispensing the R2 reagent in the reagent-containing assembly 300 installed in the reagent installing unit 7 into the cuvette 150 dispensed with the sample and the R1 reagent of the primary reaction unit 11. The reagent dispensing arm 9 includes a motor 9a, a drive transmitting part 9b connected to the motor 9a, and an arm 9d attached to the drive transmitting part 9b by way of a shaft 9c. The drive transmitting part 9b is configured to turn the arm 9d with the shaft 9c as the center by the driving force from the motor 9a, and move the arm in the up and down direction. A pipette 9e (see FIG. 1) for suctioning and discharging the R2 reagent in the reagent-containing assembly 300 is arranged at the distal end of the arm 9d. Thus, the pipette 9e is configured to suction the R2 reagent in the reagent-containing assembly 300 installed in the reagent installing unit 7, and thereafter, dispense the suctioned R2 reagent into the cuvette 150 dispensed with the sample and the R1 reagent of the primary reaction unit 11.

The reagent dispensing arm 10 (see FIGS. 1 and 2) has a function of suctioning the R3 reagent in the reagent-containing assembly installed in the reagent installing unit 6, and dispensing the suctioned R3 reagent into the cuvette 150 dispensed with the sample, the R1 reagent, and the R2 reagent of the secondary reaction unit 12. The reagent dispensing arm 10 includes a motor 10a, a drive transmitting part 10b connected to the motor 10a, and an arm 10d attached to the drive transmitting part 10b by way of a shaft 10c. The drive transmitting part 10b is configured to turn the arm 10d with the shaft 10c as the center by the driving force from the motor 10a, and move the arm in the up and down direction. A pipette 10e (see FIG. 1) for suctioning and discharging the R3 reagent in the reagent-containing assembly is arranged at the distal end of the arm 10d. That is, the pipette 10e is configured to suction the R3 reagent in the reagent-containing assembly installed in the reagent installing unit 6, and thereafter, dispense the suctioned R3 reagent into the cuvette 150 dispensed with the sample, the R1 reagent, and the R2 reagent of the secondary reaction unit 12.

As shown in FIGS. 1 and 2, the primary reaction unit 11 is arranged to rotatably transfer the cuvette 150 held by the holder 11b of the rotatable table 11a by a predetermined angle for every predetermined period (18 seconds in the present embodiment), and to stir the sample, the R1 reagent, the and the R2 reagent in the cuvette 150. That is, the primary reaction unit 11 is arranged to react the R2 reagent containing magnetic particles and the antigen in the sample in the cuvette 150. The primary reaction unit 11 is configured by a rotatable table 11a for conveying the cuvette 150 accommodating the sample, the R1 reagent, and the R2 reagent in the rotating direction, and a container conveying part 11c for stirring the sample, R1 reagent, and R2 reagent in the cuvette 150 and conveying the cuvette 150 accommodating the stirred sample, R1 reagent and R2 reagent to the BF separator 14 (see FIGS. 1 and 2) to be hereinafter described.

The rotatable table 11a is configured so as to rotatably transfer the cuvette 150 held in the holder 11b by a predetermined angle every 18 seconds. Thus, various devices (sample dispensing arm 5, reagent dispensing arms 8 and 9 etc.) of the immune analyzer 1 are controlled so as to operate on the cuvette 150 at the predetermined transferred position at a timing the cuvette is transferred to the predetermined position by the rotatable table 11a.

The container conveying part 11c is rotatably arranged at the central portion of the rotatable table 11a. The container conveying part 11c has a function of gripping the cuvette 150 held in the holder 11b of the rotatable table 11a and stirring the sample in the cuvette 150. Furthermore, the container conveying part 11c has a function of transferring the cuvette 150 accommodating the specimen obtained by stirring and incubating the sample, the R1 reagent and the R2 reagent to the BF separator 14 (see FIGS. 1 and 2).

The secondary reaction unit 12 (see FIGS. 1 and 2) has a configuration similar to the primary reaction unit 11, and is arranged to rotatably transfer the cuvette 150 held by the holder 12b of the rotatable table 12a by a predetermined angle for every predetermined period (18 seconds in the present embodiment), and to stir the sample, the R1 reagent, the R2 reagent, the R3 reagent, and the R5 reagent in the cuvette 150. That is, the secondary reaction unit 12 is arranged to react the R3 reagent containing labeled antibody and the antigen in the sample in the cuvette 150, and to react the R5 reagent containing light emitting substrates and the labeled antibody of the R3 reagent. The R5 reagent is dispensed into the cuvette 150 accommodating the sample, the R1 reagent, the R2 reagent, and the R3 reagent of the secondary reaction unit 12 by a R5 reagent dispensing arm (not shown) arranged near the secondary reaction unit 12. The secondary reaction unit 12 is configured by a rotatable table 12a for conveying the cuvette 150 accommodating the sample, the R1 reagent, the R2 reagent, the R3 reagent, and the R5 reagent in the rotating direction, and a container conveying part 12c for stirring the sample, the R1 reagent, the R2 reagent, R3 reagent, and the R5 reagent in the cuvette 150 and conveying the cuvette 150 accommodating the stirred sample etc. to the BF separator 14. The container conveying part 12c has a function of again conveying the cuvette 150 processed by the BF separator 14 to the holder 12b of the rotatable table 12. The detailed structure of the secondary reaction unit 12 is similar to the primary reaction unit 11, and thus the description thereof will be omitted.

The cuvette supplying unit 13 (see FIGS. 1 and 2) is configured to sequentially supply a plurality of cuvettes 150 to the holder 11b of the rotatable table 11a of the primary reaction unit 11.

The BF separator 14 has a function of separating the non-reacting R1 reagent (unnecessary component) and the magnetic particles from the specimen in the cuvette 150 conveyed by the container conveying part 11c of the primary reaction unit 11, and a function of separating the non-reacting R3 reagent (unnecessary component) and the magnetic particles from the specimen in the cuvette 150 (see FIG. 1) conveyed by the container conveying part 12c of the secondary reaction unit 12.

The detector 15 (see FIGS. 1 and 2) is arranged to measure the amount of antigen contained in a sample by acquiring the light generated in the reaction process of the labeled antibody bound to the antigen of the sample performed with a predetermined process and the light emitting substrate with a photo multiplier tube.

FIGS. 6 to 19 are views describing details of the reagent installing unit installed with the reagent-containing assembly according to one embodiment of the present invention and the reagent-containing assembly. The configuration of a reagent-containing assembly 300 according to one embodiment of the present invention and the reagent installing unit 7 installed with the reagent-containing assembly 300 will now be described with reference to FIGS. 6 to 19.

Figure 6:
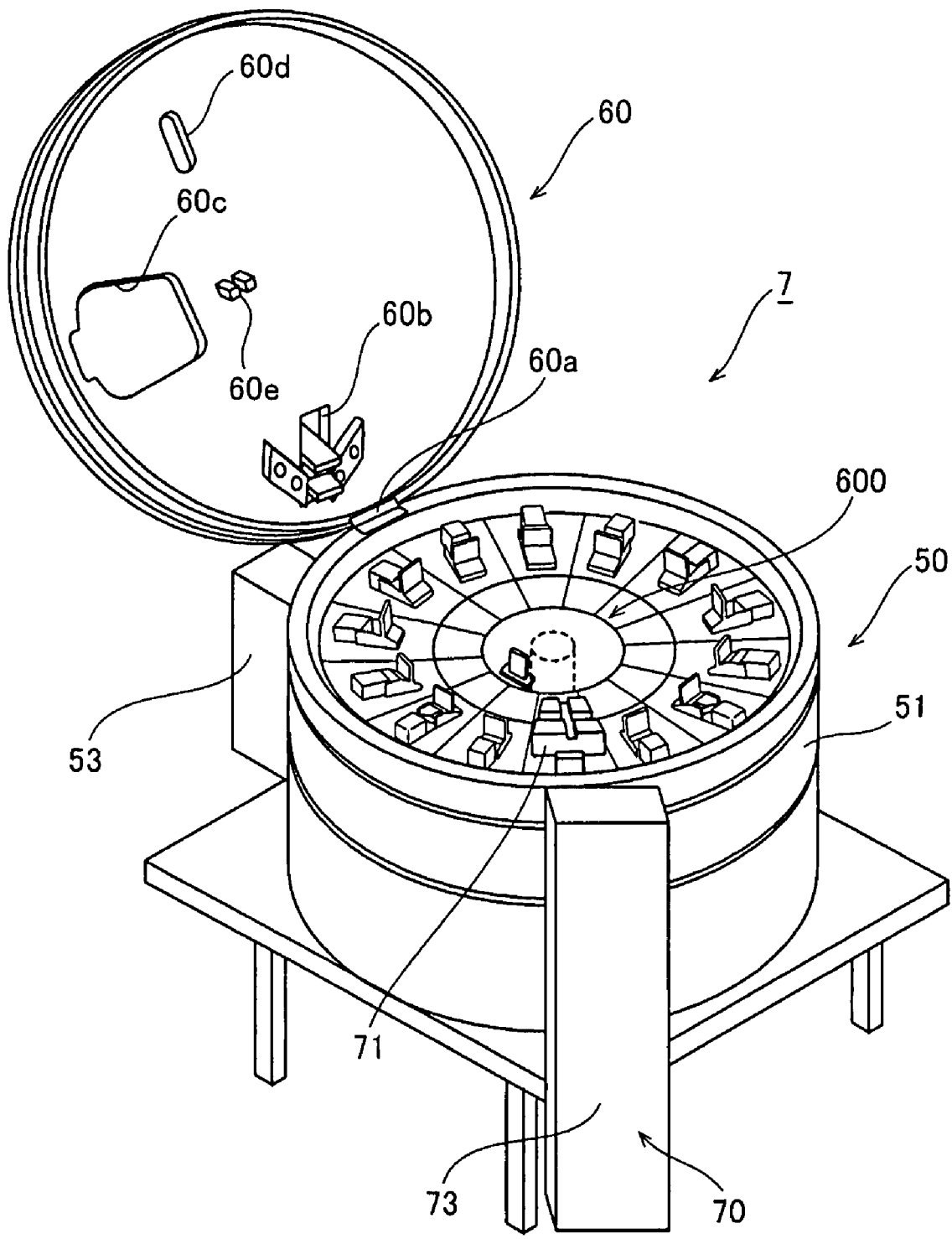
FIG. 6 is a perspective view showing an overall configuration of a reagent installing unit shown in FIG. 1.

As shown in FIG. 6, the reagent installing unit 7 includes a reagent holder 50 of cylindrical shape for holding the reagent-containing assembly 300 in a circular ring shape, a lid 60 attached to the reagent holder 50 in an openable and closable manner, and a raising and lowering unit 70 attached to the side surface (outer wall part 51) of the cylindrical reagent holder 50. A Peltier element (not shown) is also attached at the bottom of the reagent installing unit 7, and the inside of the reagent installing unit 7 is maintained at about 15° C.

Figure 7:
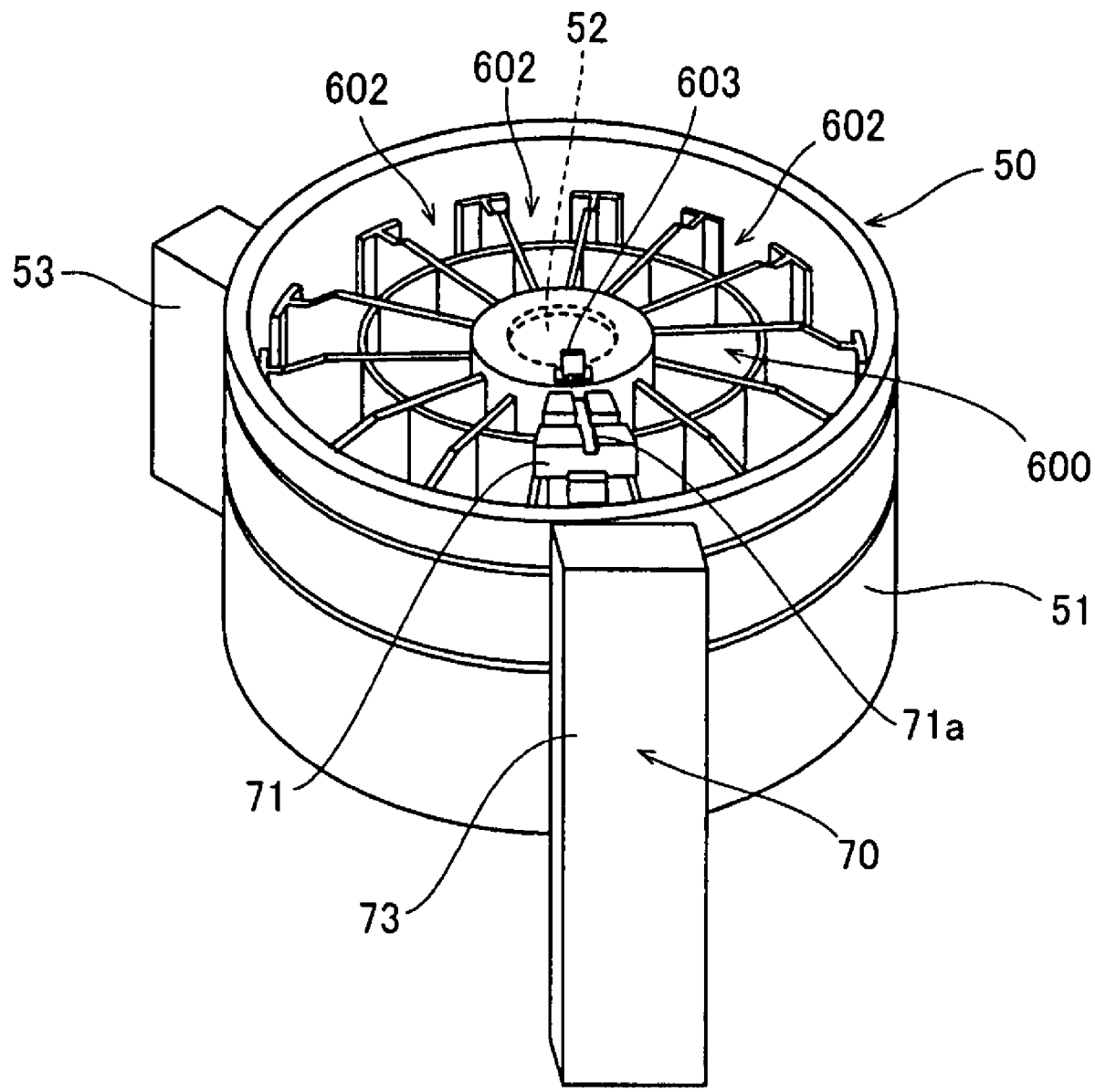
FIG. 7 is a perspective view showing a reagent holder of the reagent installing unit shown in FIG. 6.
Figure 8:
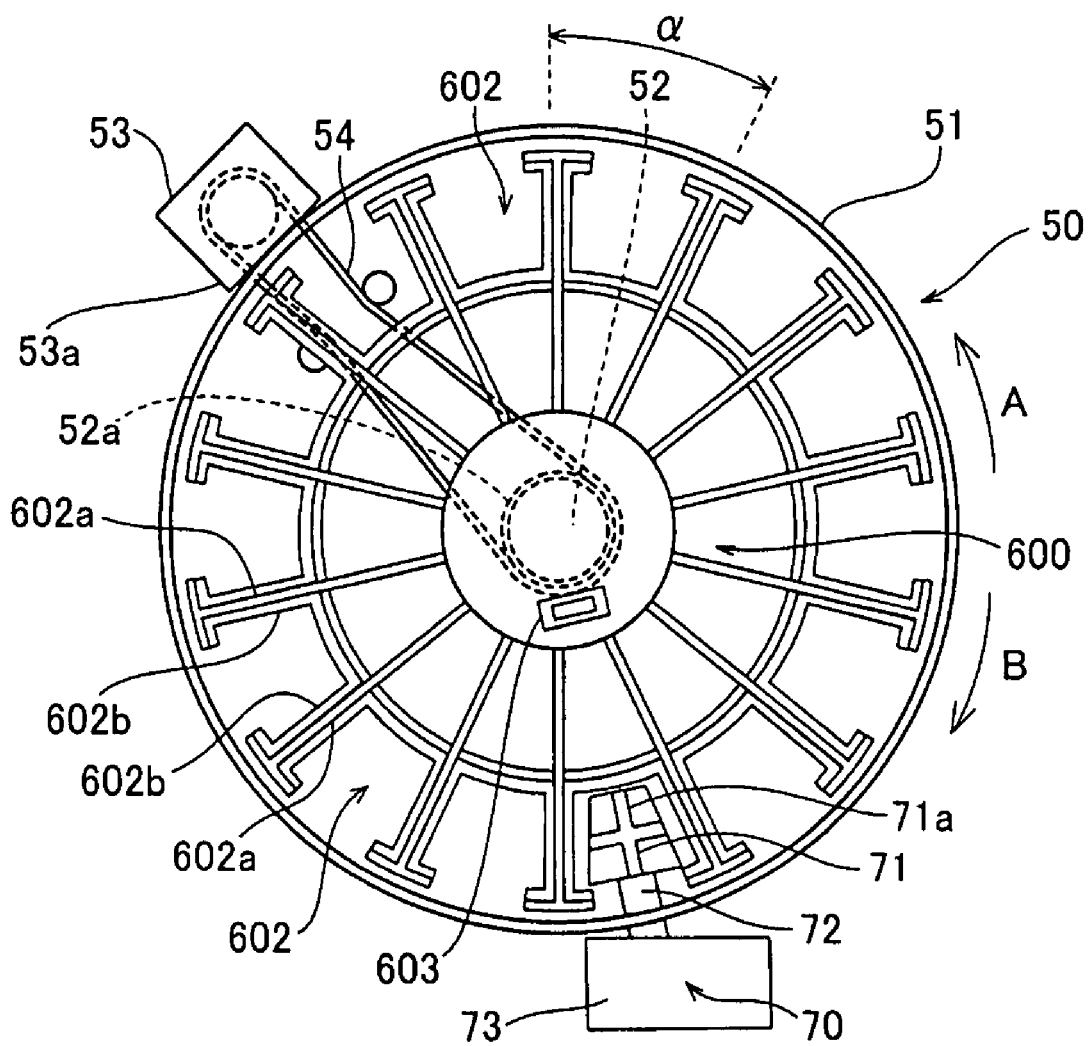
FIG. 8 is a plan view of the reagent holder of the reagent installing unit shown in FIG. 6.

As shown in FIGS. 7 and 8, the reagent holder 50 is configured similar to reagent holder 20, and includes a cylindrical outer wall part 51, a rotatable rotation shaft 52 arranged at the center, a stepping motor 53 for rotating the rotation shaft 52, and a belt 54 for transmitting the driving force of the stepping motor 53 to the rotation shaft 52 (see FIG. 8). A heat insulating material (not shown) is attached over the entire surface on the inner surface of the outer wall part 51, so that the temperature inside the reagent holder 50 is maintained at low temperature (about 15° C.). As shown in FIG. 8, the driving force of the stepping motor 53 is transmitted to the rotation shaft 52 via the belt 54 by a pulley 53a that rotates by the stepping motor 53 and a pulley 52a coaxially fixed to the rotation shaft 52.

Figure 9:
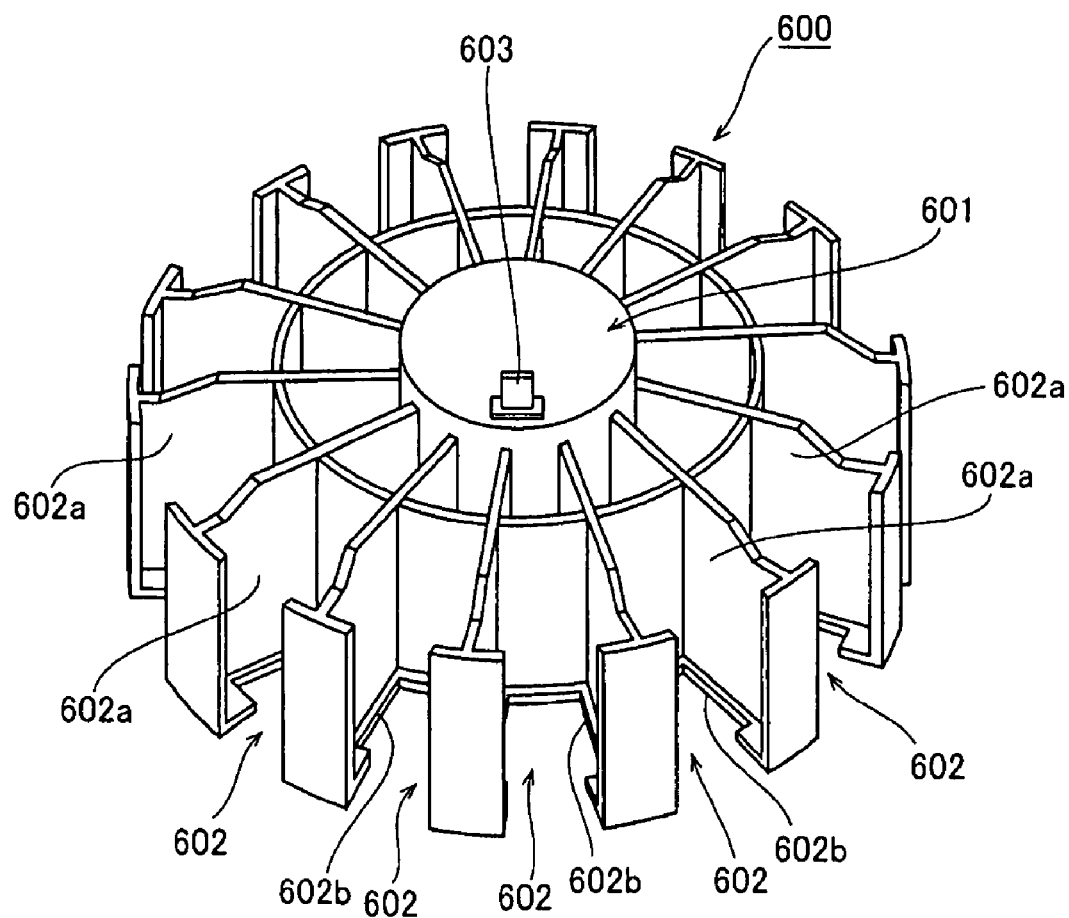
FIG. 9 is a perspective view showing a rack for holding the reagent-containing assembly according to the one embodiment of the present invention.

A rack 600 for holding a plurality of reagent-containing assemblies 300 in a circular ring form is fixedly attached to the rotation shaft 52. The rack 600 holding the reagent-containing assemblies 300 rotates when the rotation shaft 52 is rotated with the reagent-containing assemblies 300 held in the rack 600, and thus the reagent-containing assembly 300 holding the reagent to be suctioned can be moved to below a hole 60b of the lid 60 to be hereinafter described. As shown in FIG. 9, the rack 600 includes an inserting part 601, formed at the center of the rack 600, to which the rotation shaft 52 is inserted; a plurality of holders 602, formed in a circular ring form with the inserting part 601 as the center, for holding the reagent-containing assembly 300, and an origin detection strip 603 arranged so as to project above the inserting part 601. The holder 602 is configured by a partition plate 602a and a supporting part 602b. The partition plate 602a is arranged in plurals at a predetermined angular interval so as to radially extend from the inserting part 601. The supporting part 602b is arranged at the lower part of the portions facing each other of the partition plates 602a and at the lower part of the inserting part 601 so as to project to the inner side. Each reagent-containing assembly 300 is arranged so that a peripheral edge of a bottom part 324 (see FIG. 16) is supported by a supporting part 602b in a space sandwiched by a pair of partition plates 602a. A mounting section 71 of the raising and lowering unit 70 for raising and lowering the reagent-containing assembly 300 is configured to be raised and lowered by having an upper part, a lower part, and an outside part in the radial direction of the holder 602 as open ends.

As shown in FIG. 8, in the present embodiment, the rotation shaft 52 is rotatable in a reciprocating manner in a direction of an arrow A and in a direction of an arrow B by driving the stepping motor 53. In order to stir the R2 reagent (magnetic particles) installed in the reagent installing unit 7, the rack 600 holding the reagent container 310 (reagent-containing assembly 300) accommodating the R2 reagent is rotated in a reciprocating manner in the direction of the arrow A and in the direction of the arrow B to stir the R2 reagent, thereby suppressing the R2 reagent (magnetic particles), which are particles having larger weight compared to common particles, from precipitating. Specifically, the rack 600 rotates in a reciprocating manner in an angular range of angle α (about 27 degrees) at a speed of one rotation/four sec. In other words, the rack 600 is configured such that the rotating direction reverses every 0.3 second in the angular range of angle ((about 27 degrees). The rotation angle in the direction of the arrow A and the rotation angle in the direction of the arrow B in time of stirring are set substantially equal. The rotation speed in the direction of the arrow A and the rotation speed in the direction of the arrow B are also set to be substantially equal. The rack 600 is constantly rotated in a reciprocating manner other than in time of suctioning the reagent and in time of replacing the reagent-containing assembly 300 (addition, retrieval) so that the reagent can be stirred. The rack 600 rotates in a reciprocating manner even in stand-by mode of the immune analyzer 1 (state waiting for instruction of analysis, state in which sample measuring operation is not being performed).

Figure 10:
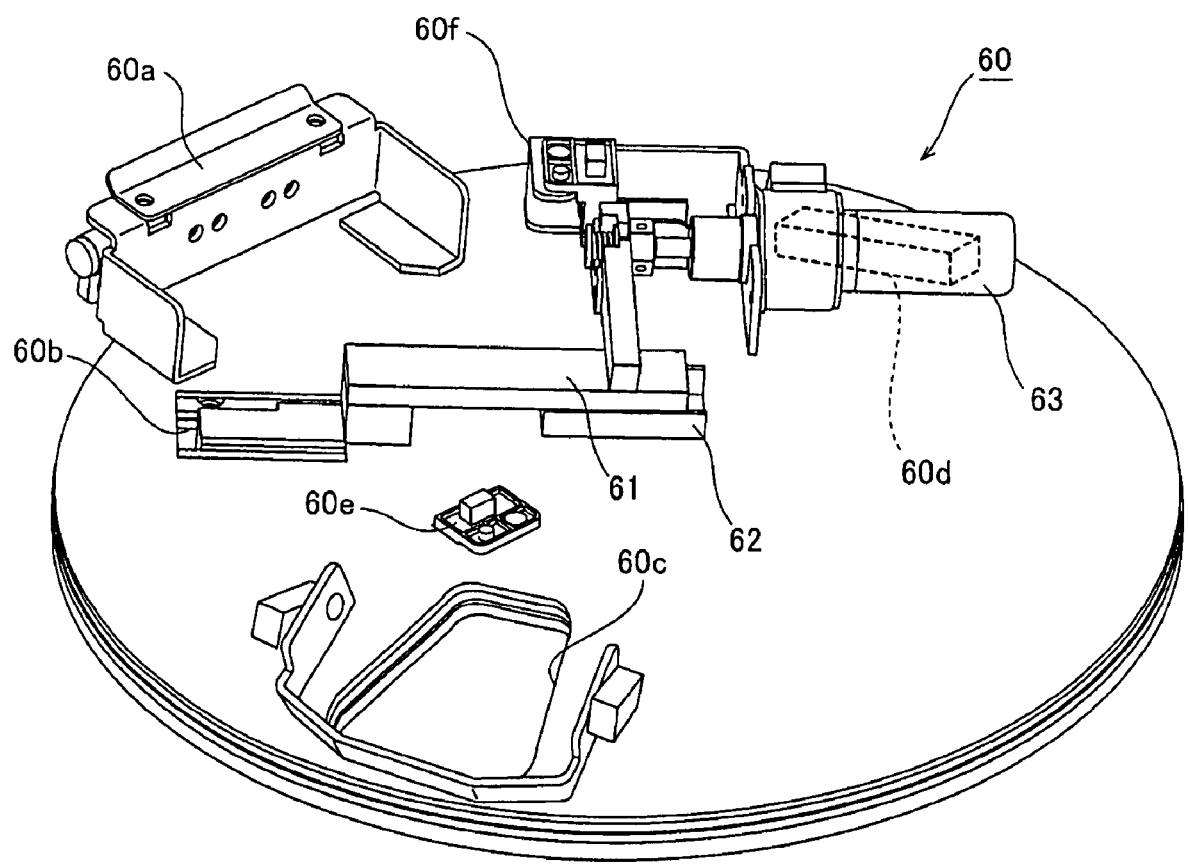
FIG. 10 is a perspective view showing a front surface of a lid of the reagent installing unit shown in FIG. 6.
Figure 11:
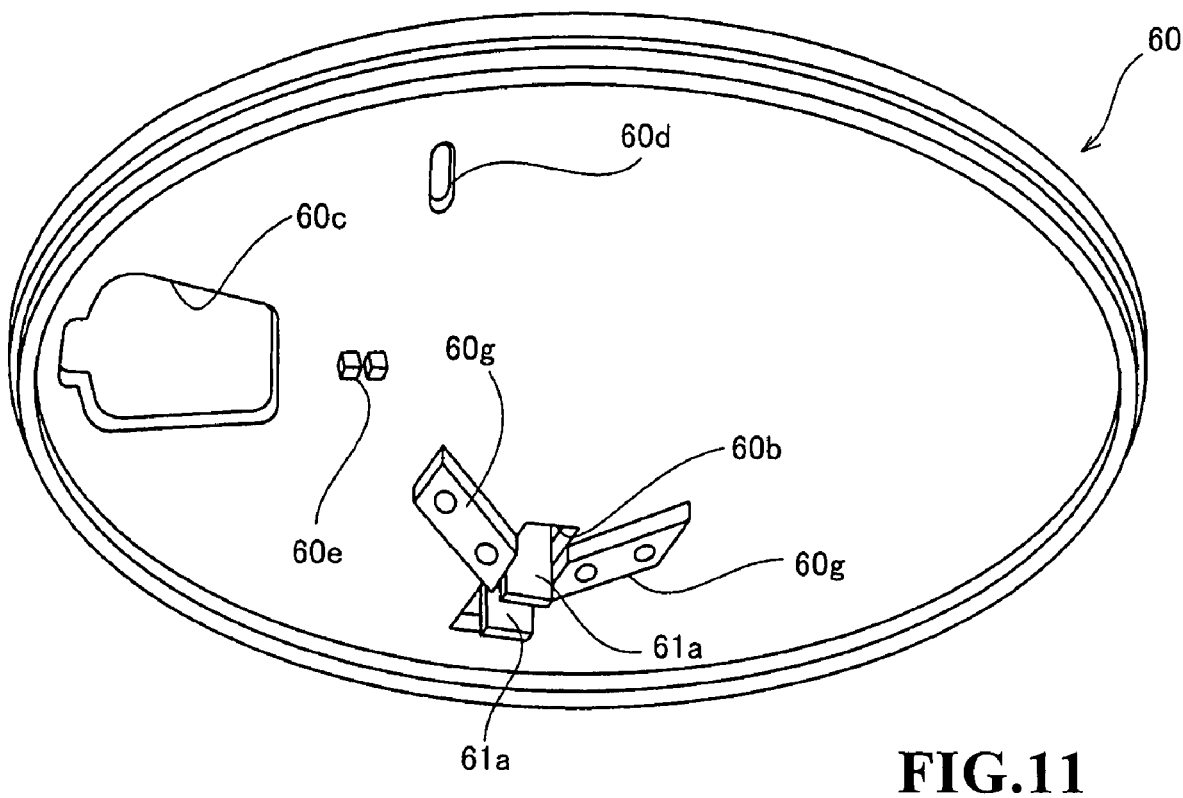
FIG. 11 is a perspective view showing a back surface of the lid of the reagent installing unit shown in FIG. 6.

As shown in FIG. 6, the lid 60 is attached in an openable and closable manner to the reagent holder 50 by way of a hinge part 60a. The lid 60 is configured to shield outside air so that the temperature in the reagent installing unit 7 is maintained at a low temperature (15(C), and so as to enable the reagent in the reagent installing unit 7 to be suctioned from the outside and the reagent-containing assembly 300 to be placed in or taken out from the reagent installing unit 7. Specifically, the lid 60 includes the hole 60b to be inserted with a pipette 9e of the reagent dispensing arm 9 when suctioning the reagent from the reagent container 310 of the reagent-containing assembly 300, and the input/output hole 60c for placing in or taking out the reagent-containing assembly 300 from the reagent installing unit 7 by the raising and lowering unit 70, as shown in FIGS. 10 and 11. Furthermore, the lid 60 includes an openable/closable member 61 for opening or closing a slide lid 370 of the reagent-containing assembly 300 arranged below the hole 60b, a linear movement guide 62 for slidably supporting the openable/closable member 61, and the stepping motor 63 for driving the openable/closable member 61 in a reciprocating manner. The lid 60 is arranged with a reflection sensor 60d for detecting whether or not the reagent-containing assembly 300 is held in the holder 602 of the rack 600, a transmissive origin detection sensor 60e for detecting an origin position of the rack 600, and a transmissive sensor 60f for detecting an origin position of the openable/closable member 61. The sensor 60*d* is arranged on the front surface side of the lid 60 so that light can be irradiated towards the back surface side of the lid 60, and the origin detection sensor 60*e* is arranged on the back surface side of the lid 60. The transmissive sensor 60*f* is arranged on the front surface side of the lid 60.

As shown in FIG. 11, the openable/closable member 61 includes a two-forked engagement strip 61*a*, similar to an openable/closable member 31. When the reagent-containing assembly 300 is arranged below the hole 60*b* with the slide lid 370 closed, the engagement strip 373 (see FIG. 12) of the slide lid 370 of the reagent-containing assembly 300 is positioned between the two-forked engagement strips 61*a* of the openable/closable member 61. A pair of guide strips 60*g* is attached near the hole 60*b* of the back surface of the lid 60. The pair of guide holes 60*g* has a function of contacting the engagement strip 373 of the slide lid 370 and guiding the same when arranged below the hole 60*b* with the slide lid 370 of the reagent-containing assembly 300 opened, thereby positioning the engagement strip 373 of the slide lid 370 between the two-forked engagement strips 61*a* of the openable/closable member 61.

The reflection sensor 60*d* is configured to detect whether or not the reagent-containing assembly 300 is held in the holder 602 of the rack 600. The transmissive origin detection sensor 30*e* has a function of detecting the origin detection strip 603 arranged in the rack 600 to detect the origin position of the rotating rack 600.

As shown in FIGS. 7 and 8, the raising and lowering unit 70 is arranged to place in and take out the reagent-containing assembly 300 in the reagent installing unit 7. The raising and lowering unit 70 includes the mounting section 71 to be mounted with the reagent-containing assembly 300, the arm 72 for supporting the mounting section 71, and a driving section 73 for sliding the arm 72 in the up and down direction. A cross-shaped groove 71*a* that engages ribs 325 arranged at the bottom 324 of the reagent container holder 320 of the reagent-containing assembly 300 is formed in the mounting section 71. The arm 72 has a function of moving the mounting section 71 in the up and down direction by the driving force of the driving section 73 arranged exterior to the reagent holder 50 by way of a hole (not shown) extending in the vertical direction on the outer wall part 51. The raising and lowering unit 70 lowers the mounting section 71 with the reagent-containing assembly 300 mounted on the mounting section 71, so that the reagent-containing assembly 300 can be held by the rack 600. The raising and lowering unit 70 also moves the mounting section 71 upward from below the reagent-containing assembly 300 held by the rack 600 to lift the reagent-containing assembly 300 held by the rack 600, so that the reagent-containing assembly 300 can be taken out from the input/output hole 60*c* of the lid 60.

The reagent installing unit 6 has a configuration similar to the reagent installing unit 7 except for that two openable/closable mechanisms are arranged on the lid 30 to open and close two slide lids 280 and 290 (see FIG. 20) of the reagent-containing assembly 200 in correspondence to the reagent-containing assembly 200 held by the reagent holder 6 including two reagent containers of a reagent container 210 for accommodating the R1 reagent and a reagent container 220 (see FIG. 20) for accommodating the R2 reagent, and thus the description thereof will be omitted.

The reagent-containing assembly 300 according to the present embodiment will now be described in detail. As shown in FIGS. 12 to 19, the reagent-containing assembly 300 according to the present embodiment includes a reagent container 310 accommodating the R2 reagent, a reagent container holder 320 for holding the reagent container 310, and a case 330 to be attached to the reagent container holder 320 so as to cover the reagent container 310.

Figure 15:
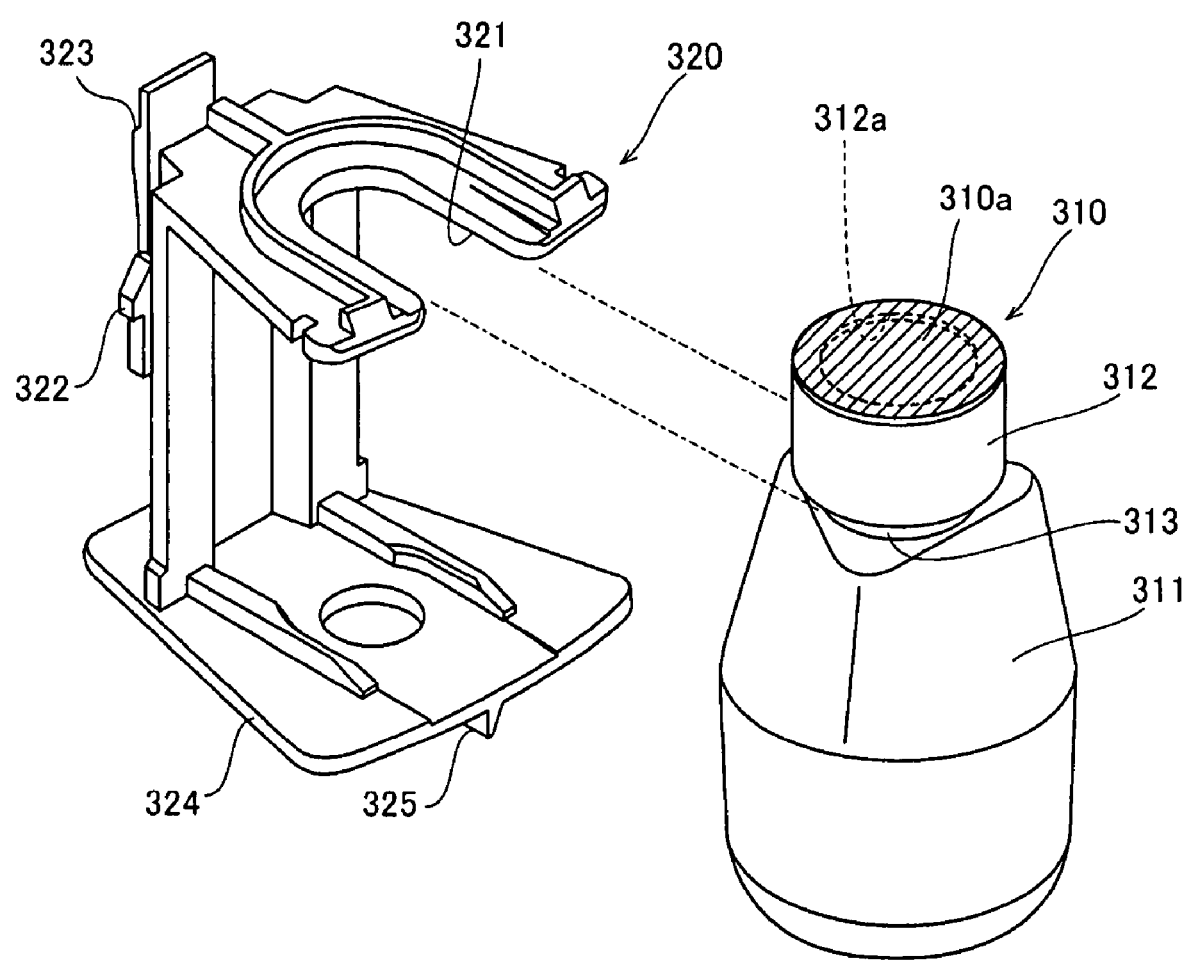
FIG. 15 is an exploded perspective view of the reagent container holder and a reagent container of the reagent-containing assembly according to the one embodiment.
Figure 19:
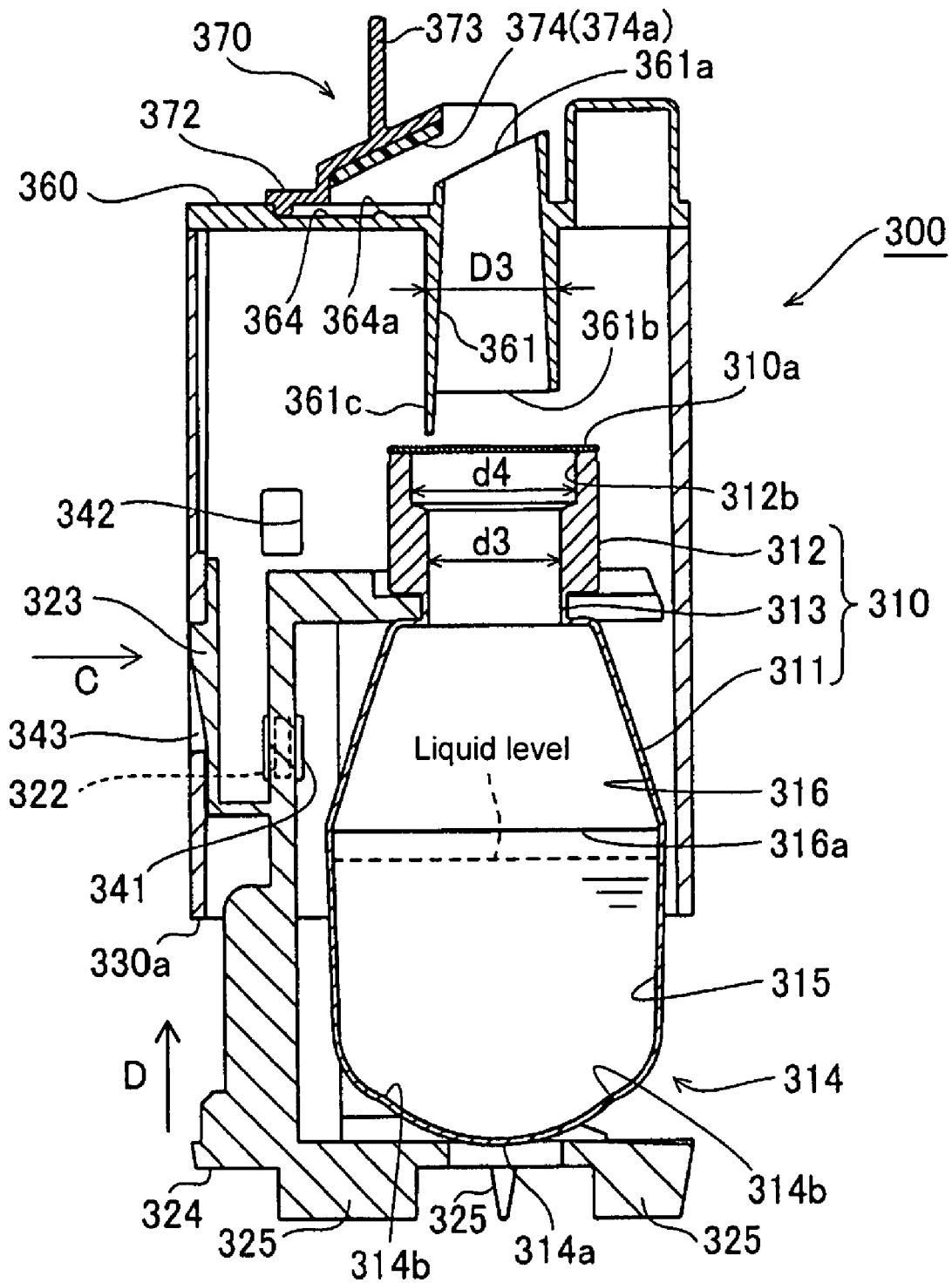
FIG. 19 is a cross sectional view showing an unused state of the reagent-containing assembly according to the one embodiment.

The reagent container 310 is made of high density polystyrene. As shown in FIG. 15, the reagent container 310 is sealed by attaching an aluminum seal 310*a* to the opening 312*a* so that deterioration, leakage etc. of the reagent accommodated in the reagent container 310 are suppressed before use (when supplied to the user). The reagent container 310 includes a body part 311 in which the reagent is accommodated, a head part 312 with the opening 312*a* for suctioning the reagent, and a neck part 313 for connecting the body part 311 and the head part 312. The head part 312 is formed into a cylindrical form, where an inner diameter $d3$ of the head part 312 (see FIG. 19) is formed to be substantially equal to an outer diameter $D3$ (see FIG. 19) of a tubular part 361 to be hereinafter described. Furthermore, a seal accommodating portion 312*b* where the aluminum seal 310*a* is to be accommodated when the aluminum seal 310*a* sealed to the opening 312*a* is broken by a projecting portion 361*c*, as hereinafter described, is arranged near the opening 312*a* of the head part 312, as shown in FIG. 19. Specifically, an inner diameter $d4$ near the opening 312*a* of the head part 312 is formed larger than the inner diameter $d3$ of other portions of the head part 312, so that the broken aluminum seal 310*a* is accommodated in the portion having the inner diameter $d4$ (seal accommodating portion 312*b*). The neck part 313 is formed so as to constrict with respect to the head part 312 and the body part 311.

Figure 14:
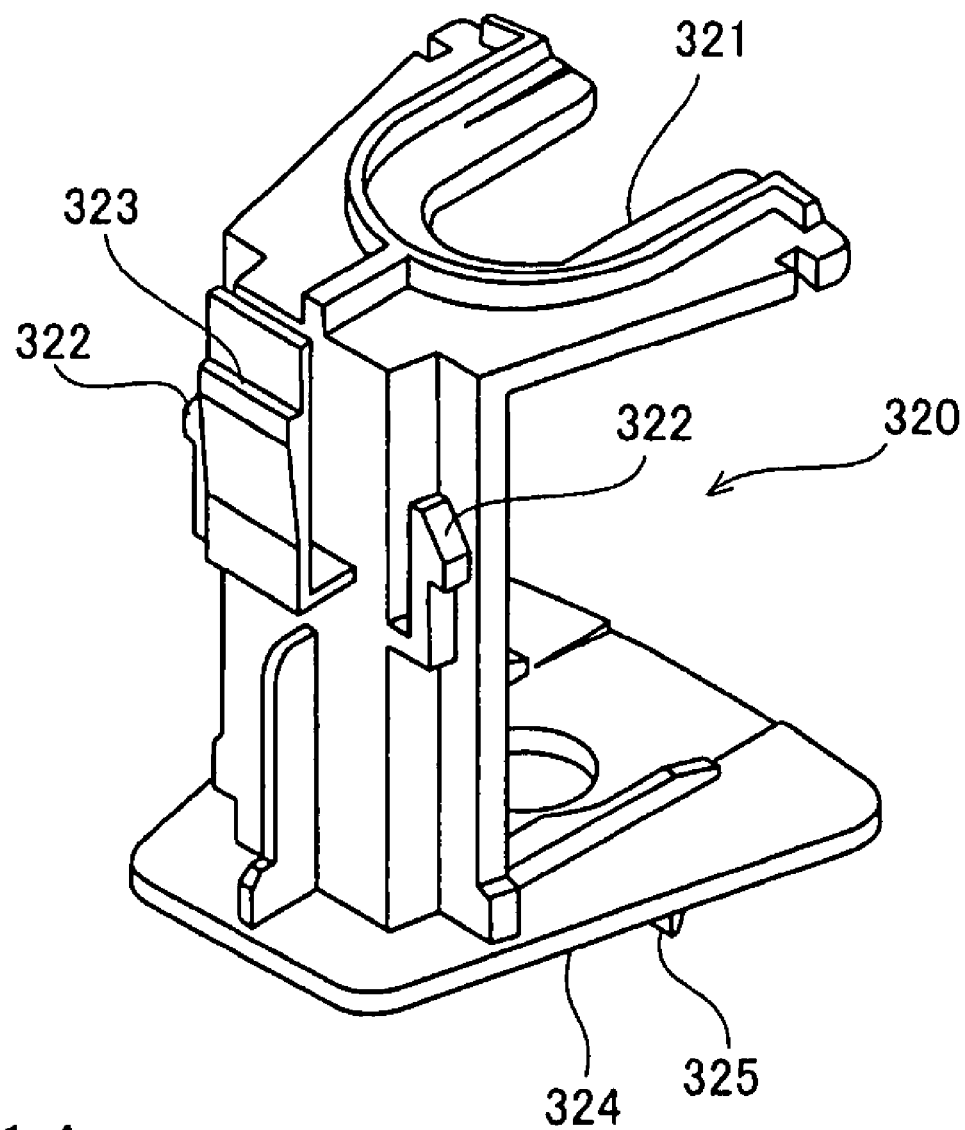
FIG. 14 is a perspective view showing a reagent container holder of the reagent-containing assembly according to the one embodiment.

As shown in FIGS. 14 and 15, the reagent container holder 320 can removably hold the reagent container 310, and includes an engagement part 321 that engages with the neck part 313 of the reagent container 310, a pair of hooks 322 for suppressing the reagent container holder 320 from moving downward with respect to the case 330, an engagement part 323 for suppressing the reagent container holder 320 from moving upward with respect to the case 330, and the ribs 325 arranged at the bottom part 324 to engage with the mounting section 71 of the raising and lowering member 70.

Figure 16:
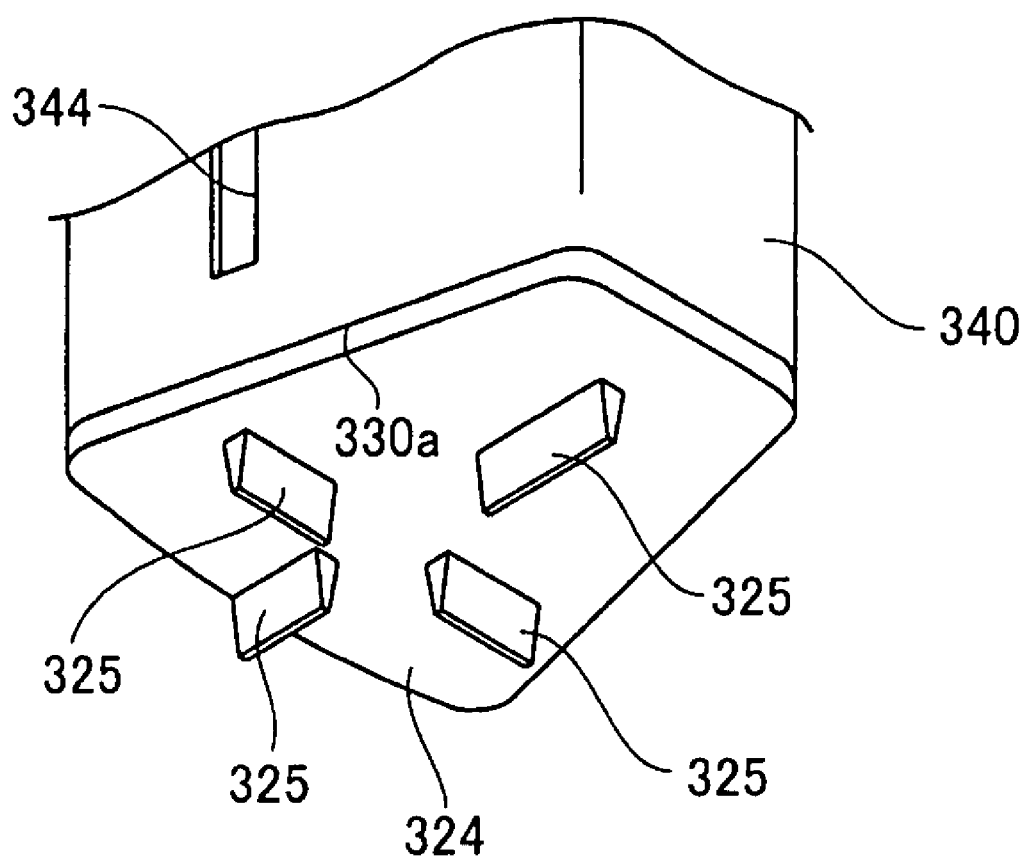
FIG. 16 is a perspective view showing a bottom surface of the reagent container holder of the reagent-containing assembly according to the one embodiment.

The engagement part 321 is configured to hold the reagent container 310 at the reagent container holder 320 by engaging the neck part 313 of the reagent container 310. The pair of hooks 322 has a function of suppressing the reagent container holder 320 from detaching from the case 330 by engaging with a pair of holes 341 and 342 formed in the case 330, to be hereinafter described. Moreover, the engagement part 323 has a function of suppressing the reagent container holder 320 from moving upward from a predetermined position with respect to the case 330 by engaging with a hole 343 formed in the case 330, to be hereinafter described. As shown in FIG. 16, the ribs 325 formed on the bottom part 324 are arranged in a cross shape.

Figure 12:
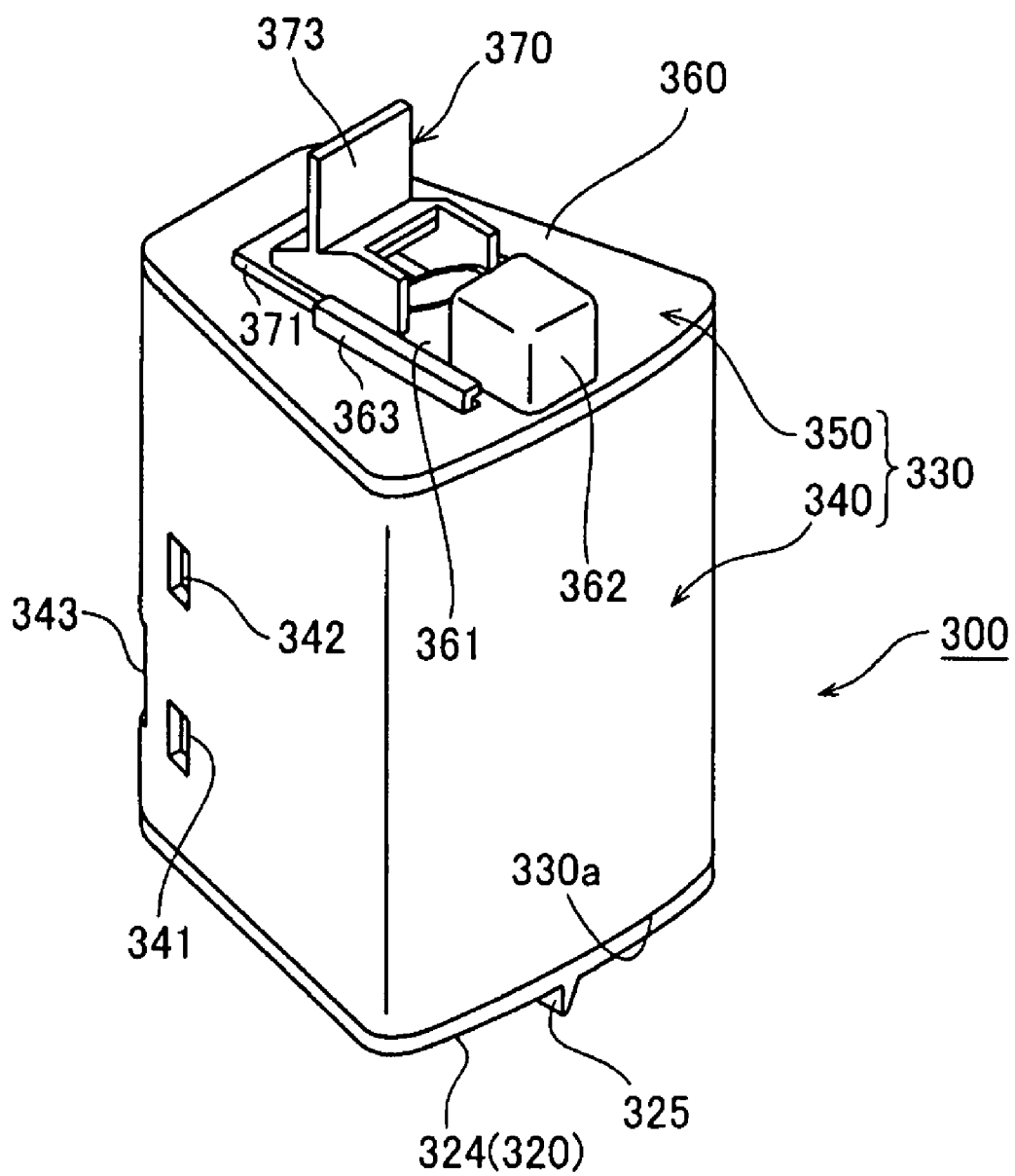
FIG. 12 is an outer appearance view of the reagent-containing assembly according to the one embodiment of the present invention.
Figure 13:
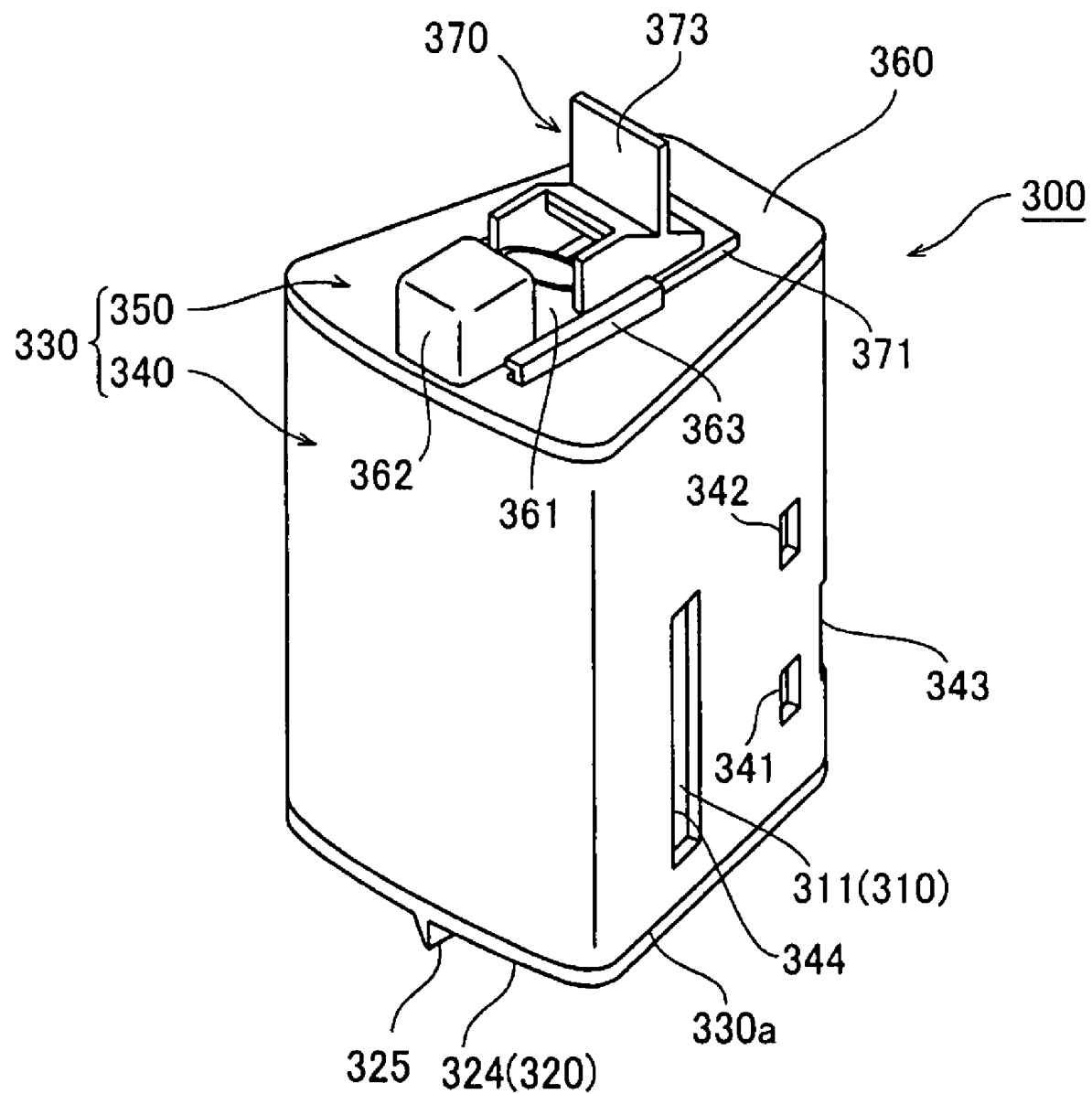
FIG. 13 is an outer appearance view of the reagent-containing assembly according to the one embodiment of the present invention.

As shown in FIGS. 12 and 13, the case 330 has a case main body 340 for covering the side surfaces of the reagent container 310 and the reagent container holder 320, and an upper lid part 350 fixedly attached to the case main body 340. The case 330 is formed into a box shape having the lower end 330*a* opened with the case main body 340 and the upper lid part 350 in a fixed state. A pair of holes 341 that engage with the pair of hooks 322 of the reagent container holder 320, a pair of holes 342 arranged with a predetermined spacing above the pair of holes 341, the hole 343 that engages with the engagement part 323 of the reagent container holder 320, and a slit 344 (see FIG. 13) formed so as to extend in an up and down direction are formed in the case main body 340. In the present embodiment, the reagent-containing assembly 300 is configured so that the amount of reagent accommodated in the reagent container 310 can be viewed through the slit 344.

Figure 17:
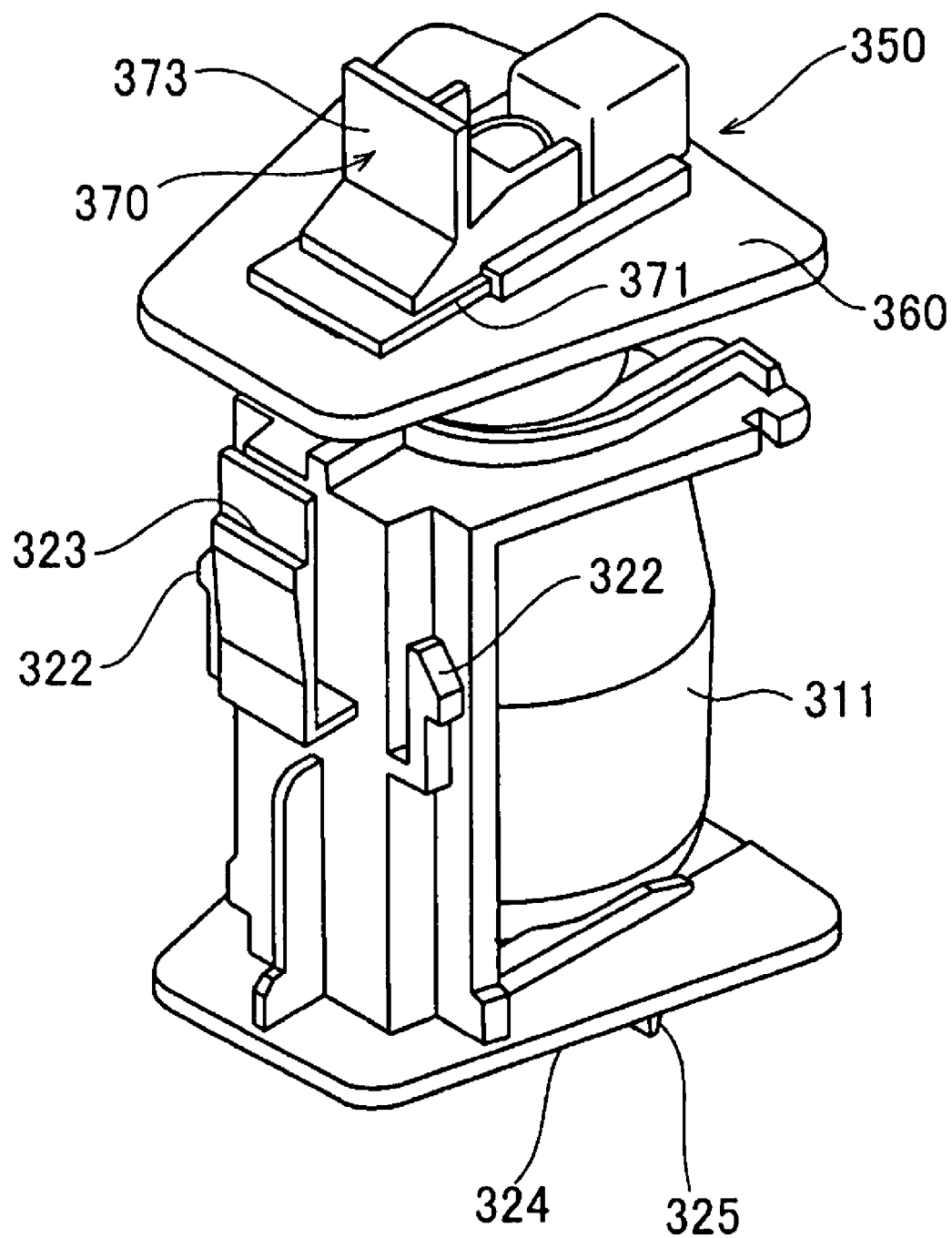
FIG. 17 is a perspective view showing the reagent container holder, the reagent container, and an upper lid part of the reagent-containing assembly according to the one embodiment.
Figure 18:
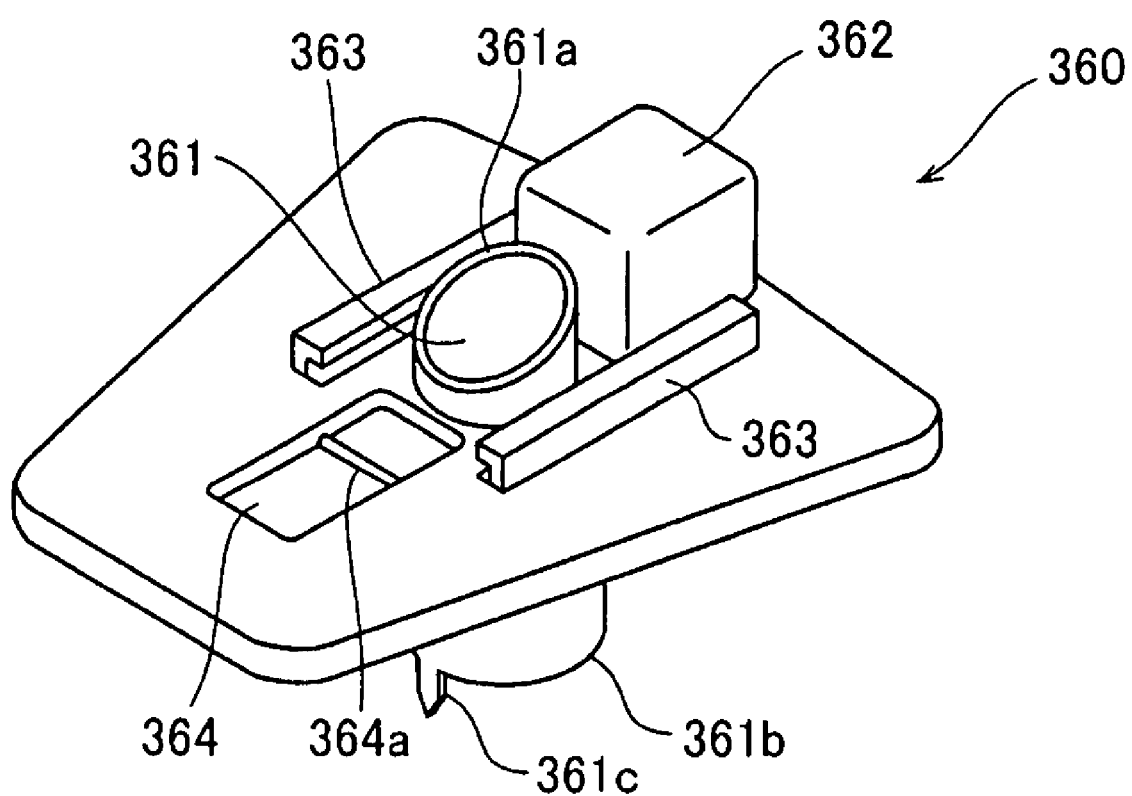
FIG. 18 is a perspective view showing an upper lid main body of the reagent-containing assembly according to the one embodiment.

As shown in FIGS. 17 to 19, the upper lid part 350 includes an upper lid main body 360, and a slide lid 370 slidably attached to the upper lid main body 360. The upper lid main body 360 has a tubular part 361 to be inserted to the opening 312a of the reagent container 310, a reflection part 362 for reflecting the light irradiated by the reflection sensor 60e arranged on the lid 60, slide rails 363 for the slide lid 370 to slide, and a concave part 364 for respectively regulating the position of the slide lid 370.

As shown in FIG. 19, the tubular part 361 is formed so that an opening end face 361a on the upper side has an inclined surface inclined by a predetermined angle from a horizontal plane. The opening end face 361b on the lower side is formed so as to be a horizontal plane. The pointed projecting portion 361c projecting downward is arranged on the opening end face 361b on the lower side. The aluminum seal 310a attached to the opening 312a is broken by the projecting portion 361c.

Furthermore, the concave part 364 has a function of regulating the movement of the slide lid 370 by contacting a projecting part 372 of the slide lid 370 and suppressing the slide lid 370 from slipping off from the upper lid main body 360. A convex shaped rib 364a that engages the projecting part 372 of the slide lid 370 when the slide lid 370 is at a position of closing the opening end face 361a on the upper side of the tubular part 361 is arranged in the concave part 364. The slide lid 370 thus can be fixed with the slide lid 370 sealing the tubular part 361.

As shown in FIG. 19, the slide lid 370 includes engagement parts 371 that engage with the slide rails 363, the projecting part 372 fitted into the concave part 364 of the upper lid main body 360, an engagement strip 373 that engages the openable/closable member 61 of the lid 60, and a contacting part 374 formed so as to have an inclined surface inclined by a predetermined angle. A plate shaped silicone sheet 374a that closely attaches to the opening end face 361a on the upper side of the tubular part 361 when the slide lid 370 seals the tubular part 361 is attached to the contacting part 374.

As shown in FIG. 19, the reagent container 310 includes a bottom part 314 formed to a smooth concave surface shape, a middle part 315 formed to a cylindrical shape, and a tapered shape part 316 formed so that the cross sectional area of the horizontal cross section gradually narrows towards the upper side from the upper end of the middle part 315. The horizontal cross section of the bottom part 314 is formed into a circular shape, and an inner shape including a distal end 314a is formed into a substantially spherical surface shape. Furthermore, a step portion 314b projecting towards the inner side is formed on the inner surface of the bottom part 314. The R2 reagent is accommodated in the reagent container 310 such that the liquid level is lower than a lower end 316a of the tapered shape part 316.

The details of the reagent-containing assembly 200 according to the present embodiment will now be described. As shown in FIGS. 20 to 29, the reagent-containing accommodating assembly 200 according to the present embodiment includes the reagent container 210 accommodating the R1 reagent, the reagent container 220 accommodating the R3 reagent, the reagent container holder 230 for holding the reagent container 210 and the reagent container 220, and a case 240 to be attached to the reagent container holder 230 so as to cover the reagent container 210 and the reagent container 220.

Figure 23:
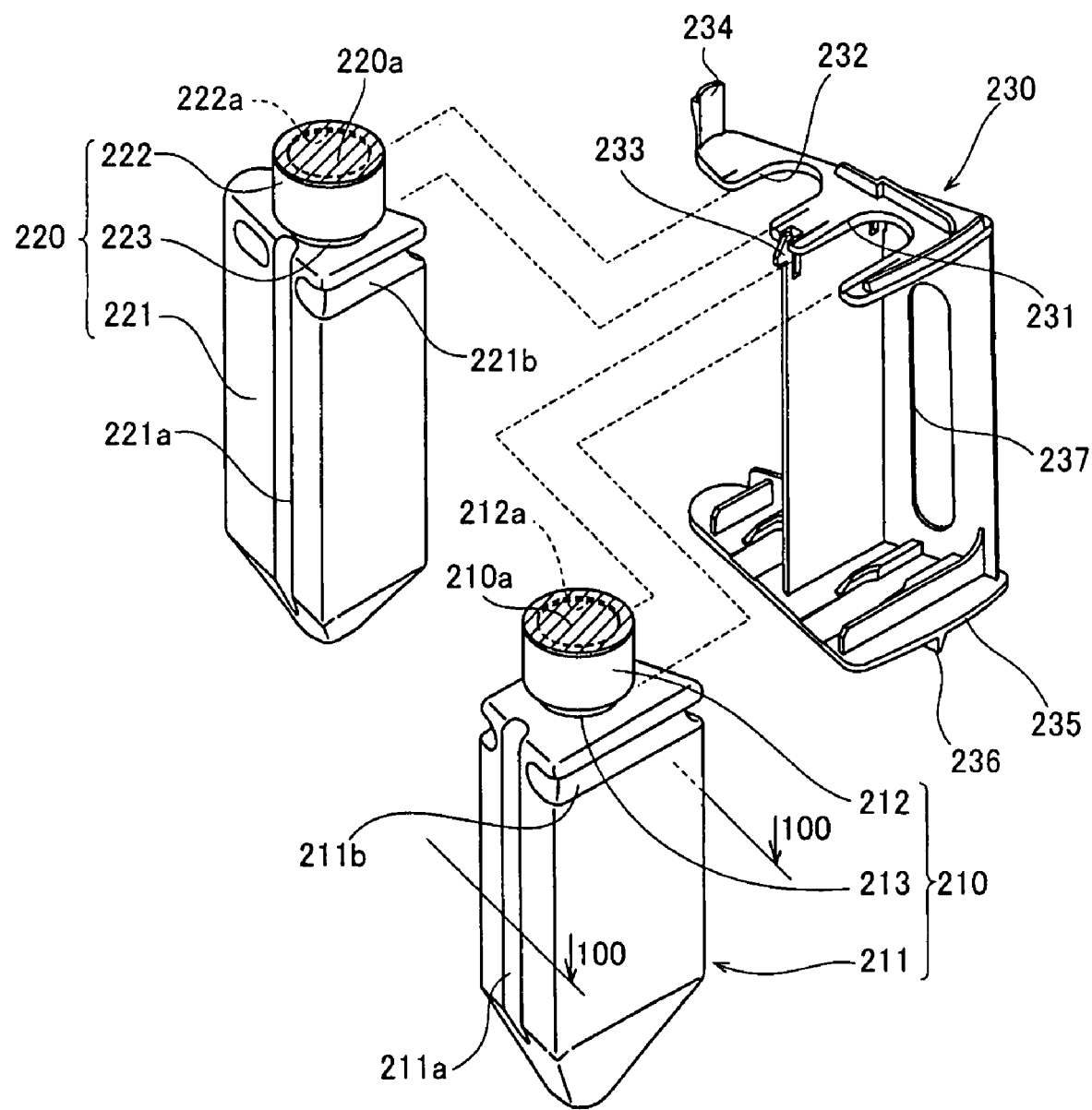
FIG. 23 is an exploded perspective view of the reagent container holders and reagent containers of the reagent-containing assembly according to the one embodiment.
Figure 25:
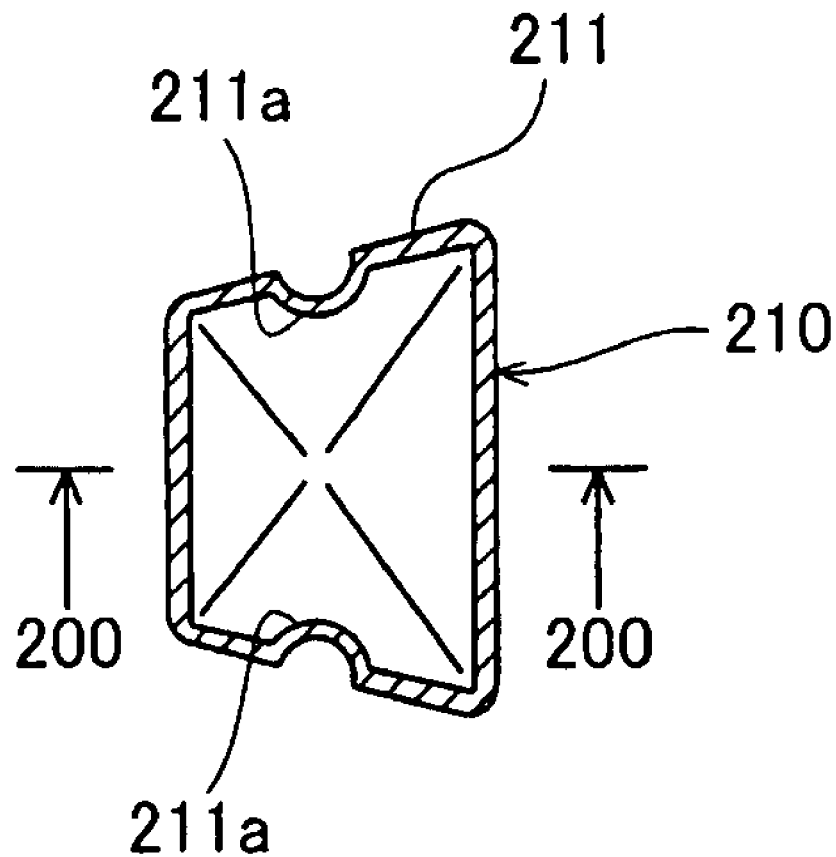
FIG. 25 is a cross sectional view taken along line 100-100 of the reagent container shown in FIG. 23.
Figure 26:
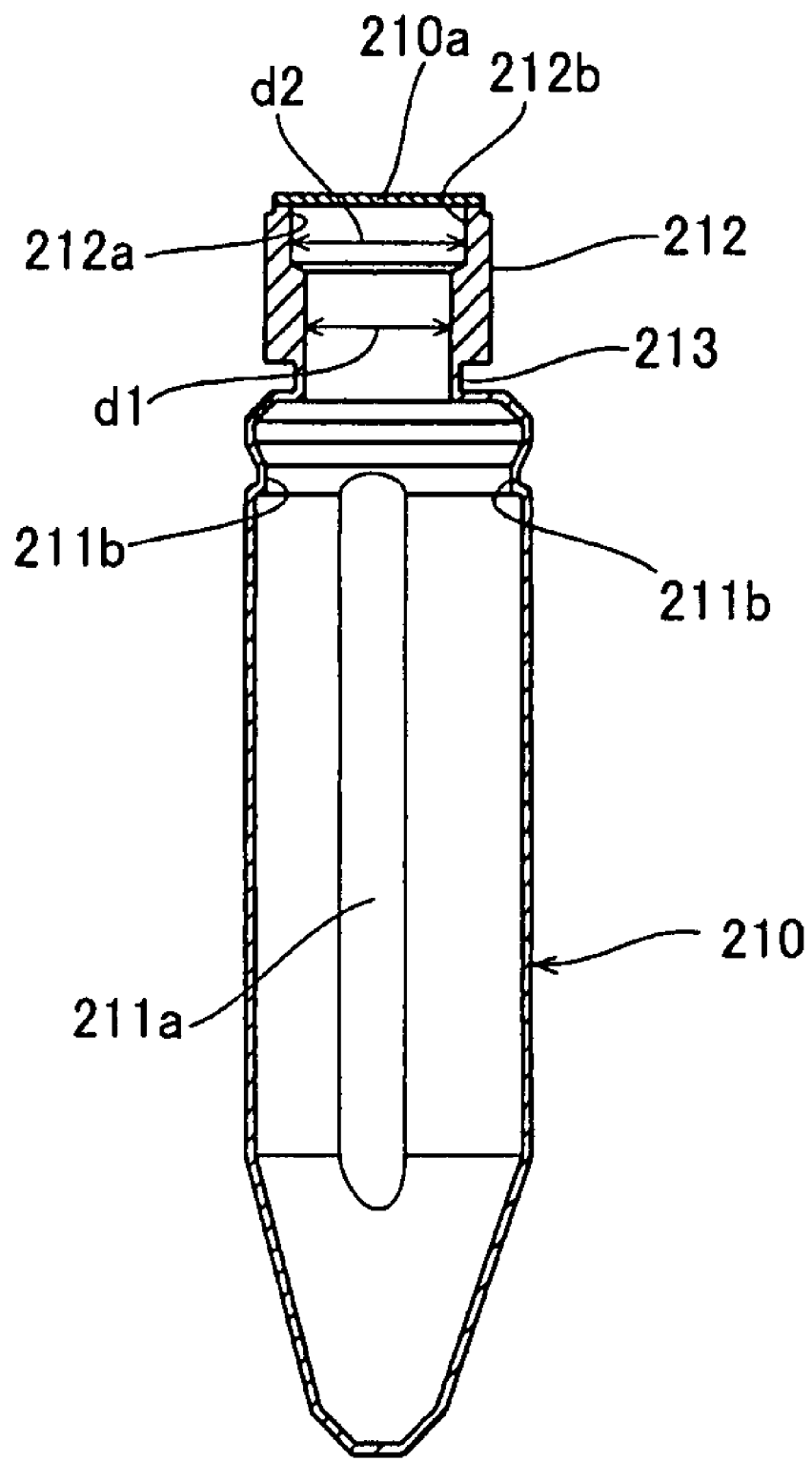
FIG. 26 is a cross sectional view taken along line 200-200 of the reagent container shown in FIG. 25.

The reagent container 210 and the reagent container 220 are made of high density polystyrene. As shown in FIG. 23, the reagent container 210 and the reagent container 220 are respectively sealed by attaching aluminum seal 210a and 220a to the opening 212a and the opening 222a to be hereinafter described, respectively, so that deterioration, leakage etc. of the reagent accommodated in the reagent container 210 and the reagent container 220 are suppressed before use (when supplied to the user). The reagent container 210 includes a body part 211 in which the reagent is accommodated, a head part 212 with the opening 212a for suctioning the reagent, and a neck part 213 for connecting the body part 211 and the head part 212. As shown in FIGS. 25 and 26, a convex portion 211a projecting towards the inner side so as to extend in the vertical direction (see FIG. 25) and a convex portion 211b projecting towards the inner side so as to extend in the horizontal direction (see FIG. 26) are formed on the inner surface of the body part 211. The head part 212 is formed into a cylindrical form, where an inner diameter d1 of the head part 212 (see FIG. 26) is formed to be substantially equal to an outer diameter D1 (see FIG. 29) of a tubular part 271 to be hereinafter described. Furthermore, a seal accommodating portion 212b where the aluminum seal 210a is to be accommodated when the aluminum seal 210a sealed to the opening 212a is broken by a projecting portion 271c, as hereinafter described, is arranged near the opening 212a of the head part 212, as shown in FIG. 26. Specifically, an inner diameter d2 near the opening 212a of the head part 212 is formed larger than the inner diameter d1 of other portions of the head part 212, so that the broken aluminum seal 210a is accommodated in the portion having the inner diameter d2 (seal accommodating portion 212b). The neck part 313 is formed so as to constrict with respect to the head part 212 and the body part 211. Furthermore, the reagent container 220 also includes a body part 221, a head part 222 and a neck part 223, similar to the reagent container 210, and includes convex portions 221a projecting towards the inner side so as to extend in the vertical direction, convex portions 221b projecting towards the inner side so as to extend in the horizontal direction, and a seal accommodating portion (not shown), as shown in FIG. 23. The inner diameter of the head part 222 of the reagent container 220 is formed substantially equal to the outer diameter D2 of the tubular part 272 to be hereinafter described (see FIG. 29).

Figure 22:
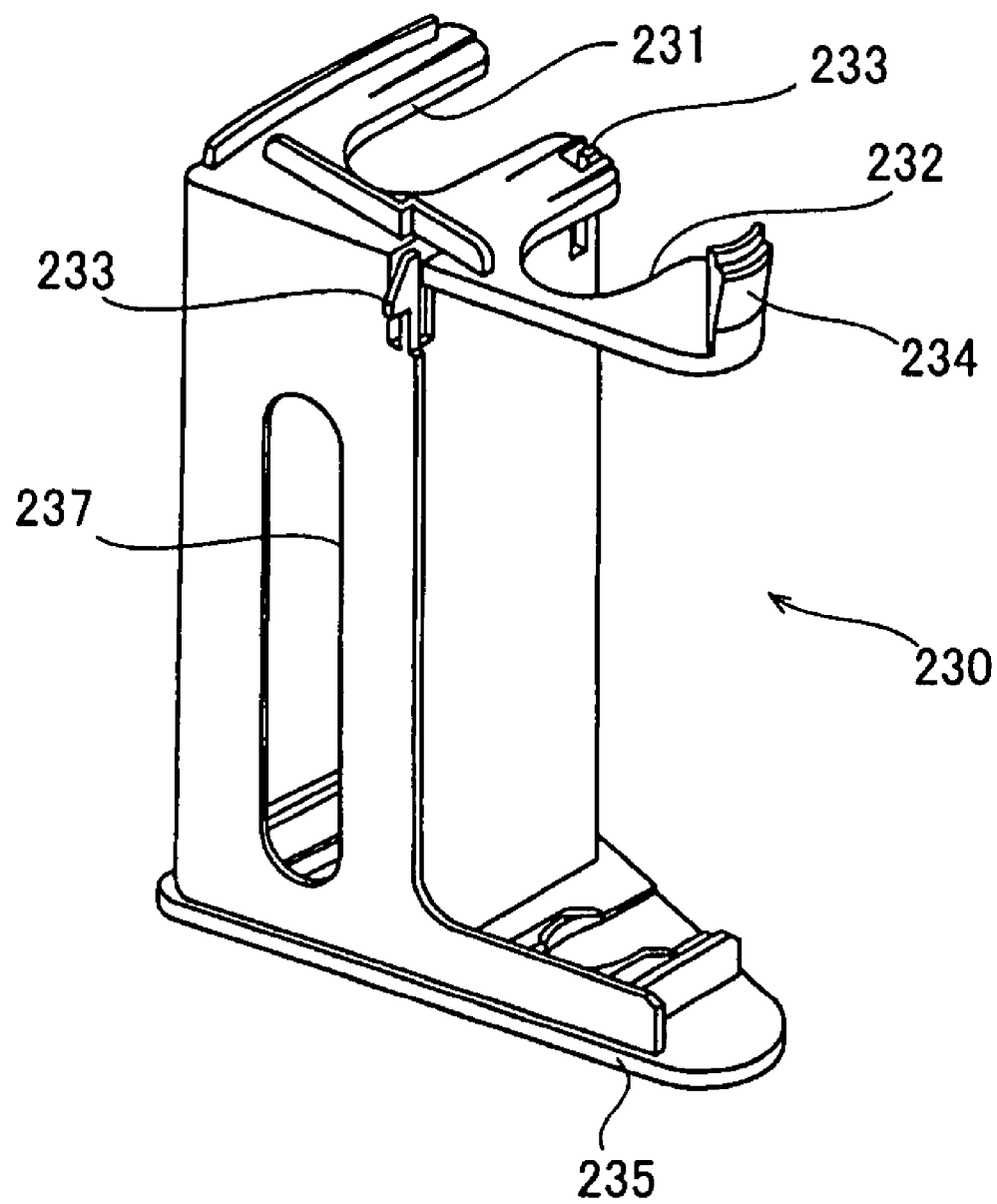
FIG. 22 is a perspective view showing a reagent container holder of the reagent-containing assembly according to the one embodiment.

The reagent container holder 230 can removably hold the reagent container 210 and the reagent container 220, and includes an engagement part 231 that engages with the neck part 213 of the reagent container 210, an engagement part 232 that engages with the neck part 223 of the reagent container 220, a pair of hooks 232 for suppressing the reagent container holder 230 from moving downward with respect to the case 240, an engagement part 234 for suppressing the reagent container holder 230 from moving upward with respect to the case 240, ribs 236 arranged at the bottom part 235 to engage with grooves 41a of the mounting section 41 of the raising and lowering unit 40, and a slit 237 formed at a position corresponding to a slit 254 of a case main body 250, to be hereinafter described, as shown in FIGS. 22 and 23.

Figure 24:
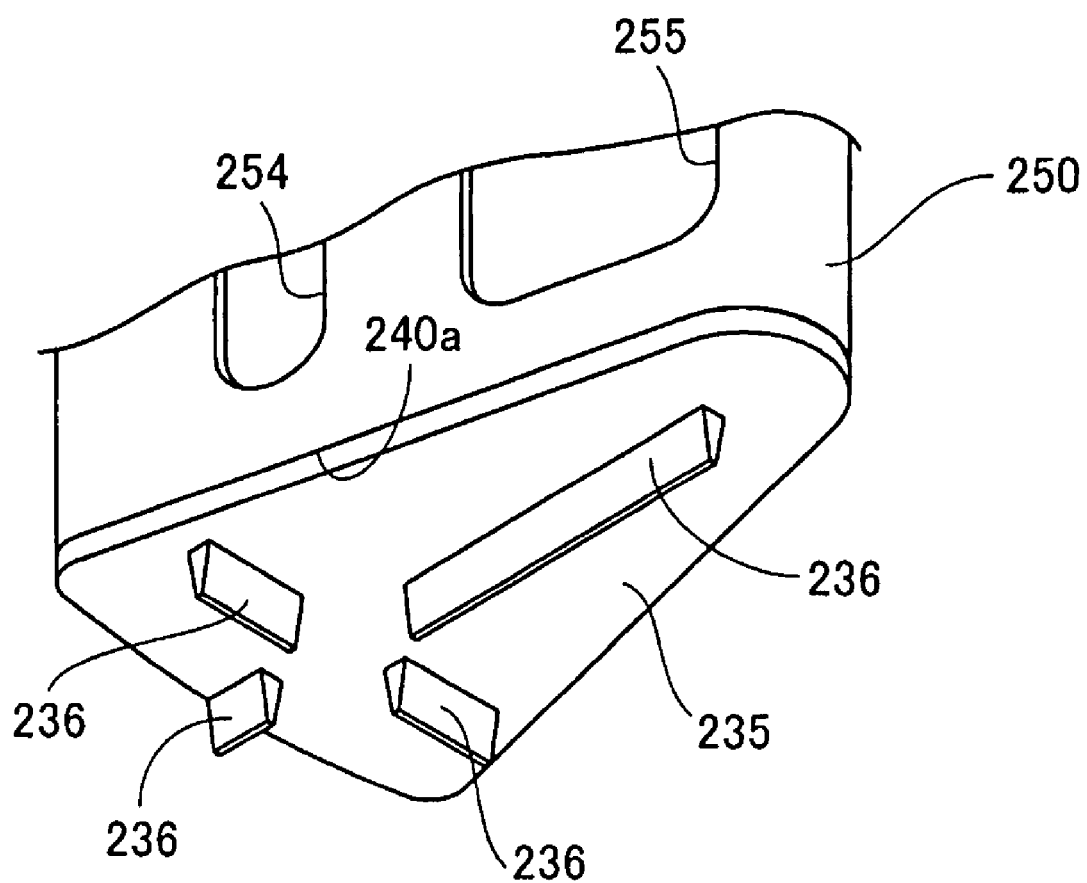
FIG. 24 is a perspective view showing a bottom surface of the reagent container holder of the reagent-containing assembly according to the one embodiment.

The engagement part 231 and the engagement part 232 are respectively formed with a concave part having a width substantially equal to the diameter of the neck part 213, 223 so as to engage with the neck part 213 and 223 of the reagent container 210 and the reagent container 220. The reagent container 210 and the reagent container 220 are held by the reagent container holder 230 by engaging the neck parts 213, 223 with the engagement parts 231, 232. The pair of hooks 233 has a function of suppressing the reagent container holder 230 from detaching from the case 240 by engaging with a pair of holes 251 and 252 formed in the case 240, to be hereinafter described. Moreover, the engagement part 234 has a function of suppressing the reagent container holder 230 from moving upward from a predetermined position with respect to the case 240 by engaging with a hole 253 formed in the case 240, to be hereinafter described. As shown in FIG. 24, the ribs 236 formed on the bottom part 235 is arranged in cross shape.

Figure 20:
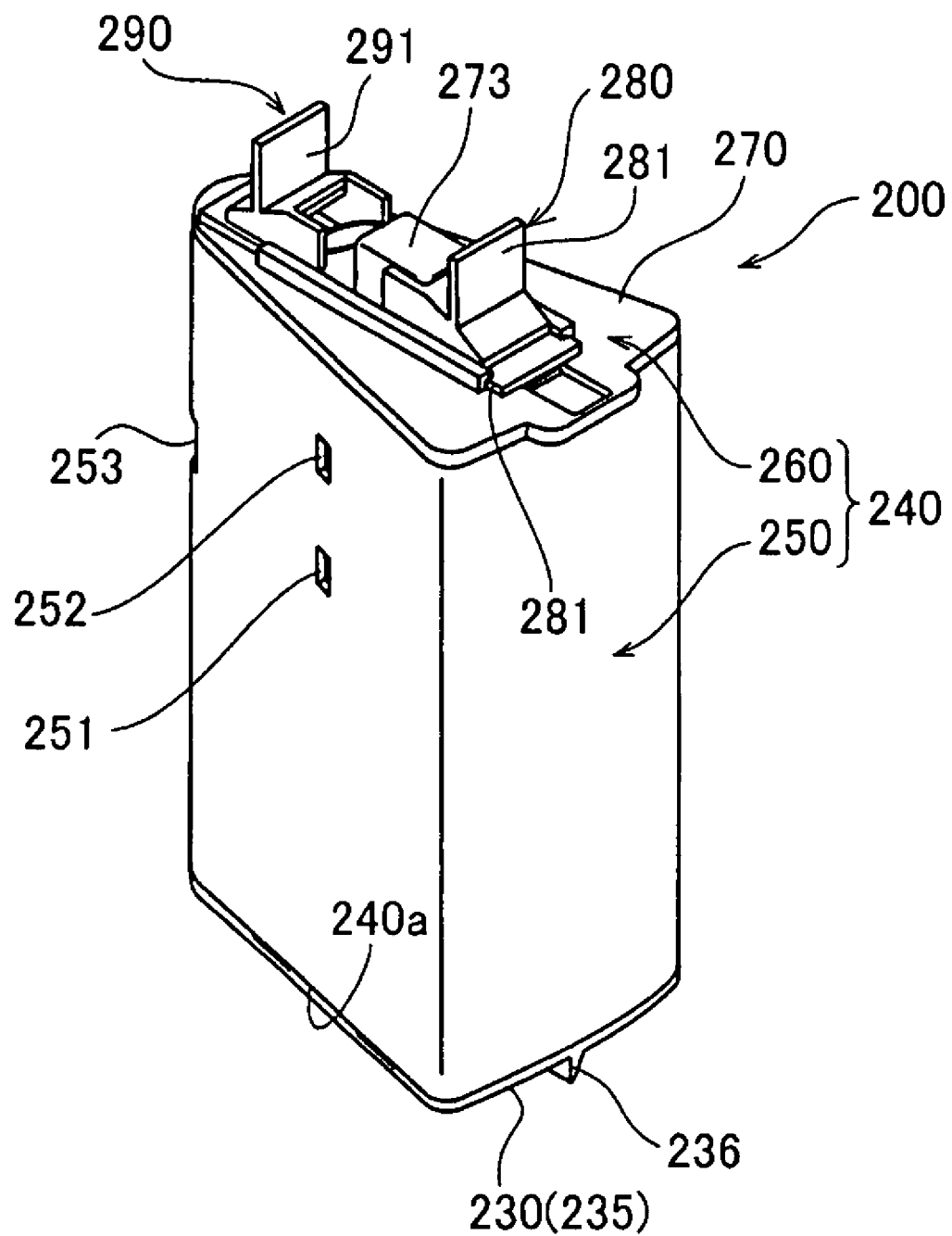
FIG. 20 is an outer appearance view of a reagent-containing assembly according to one embodiment of the present invention.
Figure 21:
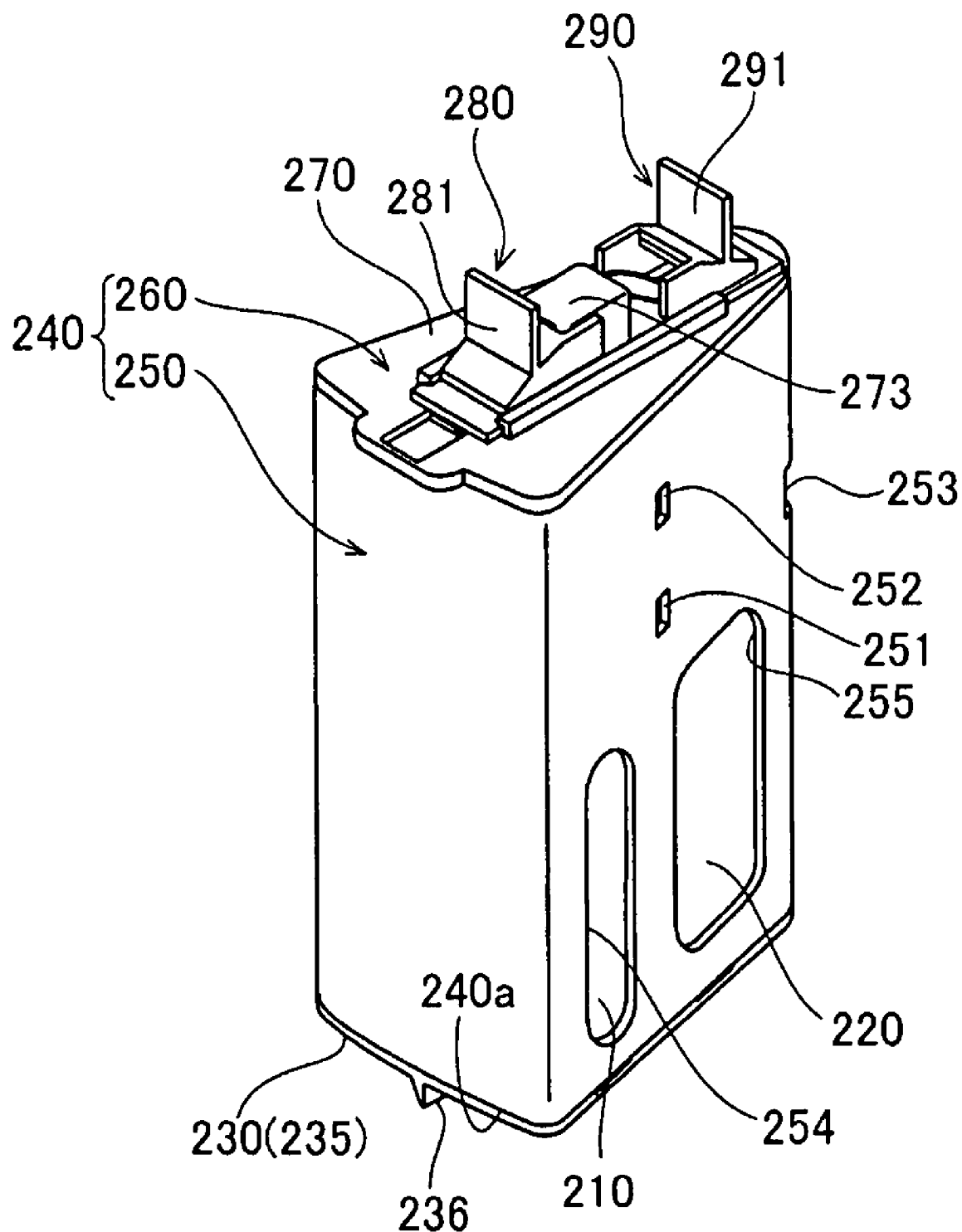
FIG. 21 is an outer appearance view of the reagent-containing assembly according to the one embodiment of the present invention.

As shown in FIGS. 20 and 21, the case 240 has a case main body 250 for covering the side surfaces of the reagent container 210, the reagent container 220, and the reagent container holder 230, and an upper lid part 260 fixedly attached to the case main body 250. The case 240 is formed into a box shape having the lower end 240a opened with the case main body 250 and the upper lid part 260 in a fixed state. A pair of holes 251 that engage with the pair of hooks 233 of the reagent container holder 230, a pair of holes 252 arranged with a predetermined spacing above the pair of holes 251, the hole 253 that engages with the engagement part 234 of the reagent container holder 230, and slits 254 and 255 formed so as to extend in the up and down direction are formed in the case main body 250. In the present embodiment, the reagent-containing assembly 200 is configured so that the amount of reagent accommodated in the reagent container 210 can be viewed through the slit 254 and the slit 237 of the reagent container holder 230. Furthermore, the reagent-containing assembly 200 is configured so that the amount of reagent accommodated in the reagent container 220 can be viewed through the slit 255.

Figure 27:
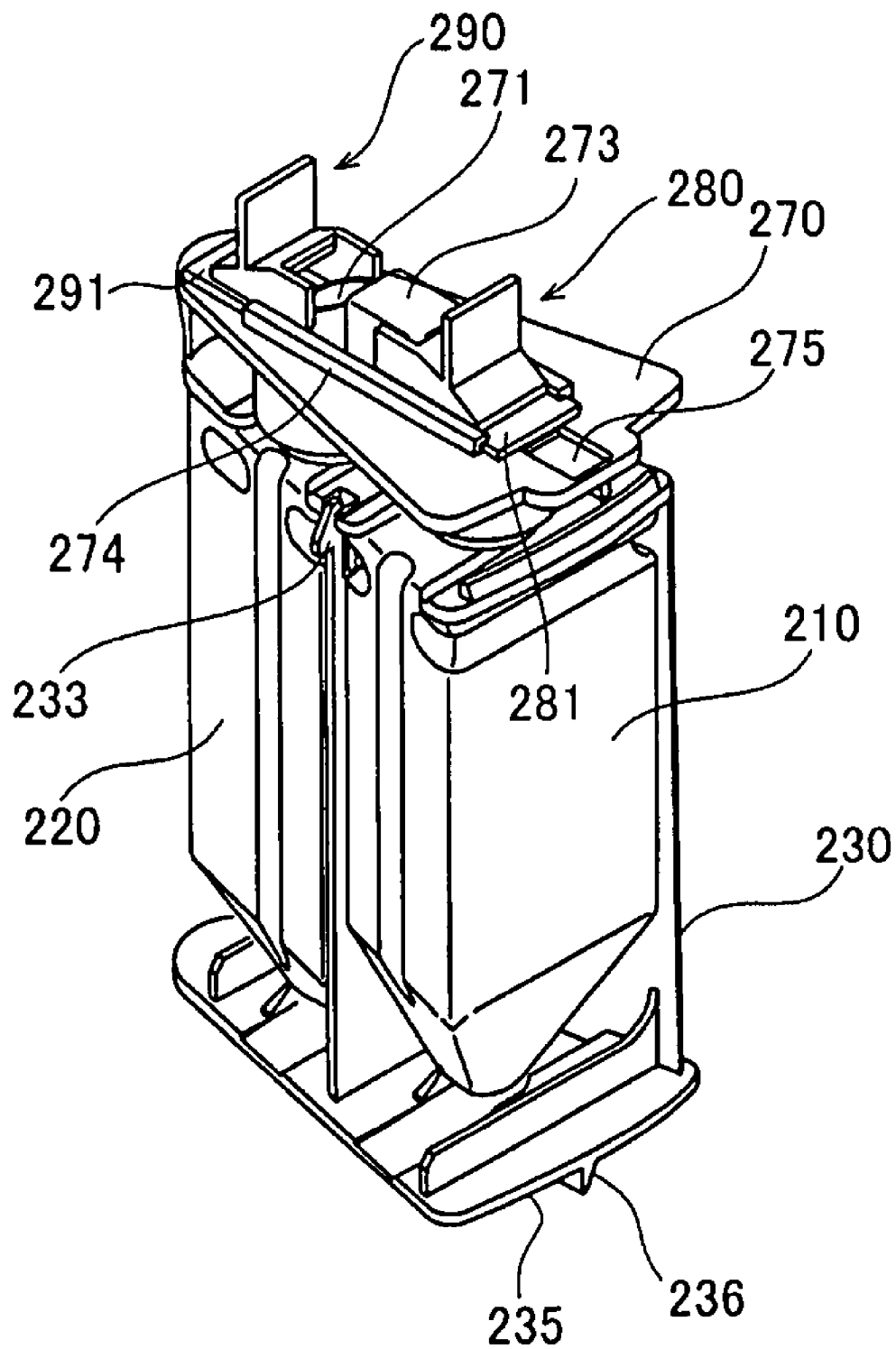
FIG. 27 is a perspective view of the reagent container holder, the reagent container, and the upper lid part of the reagent-containing assembly according to the one embodiment.
Figure 28:
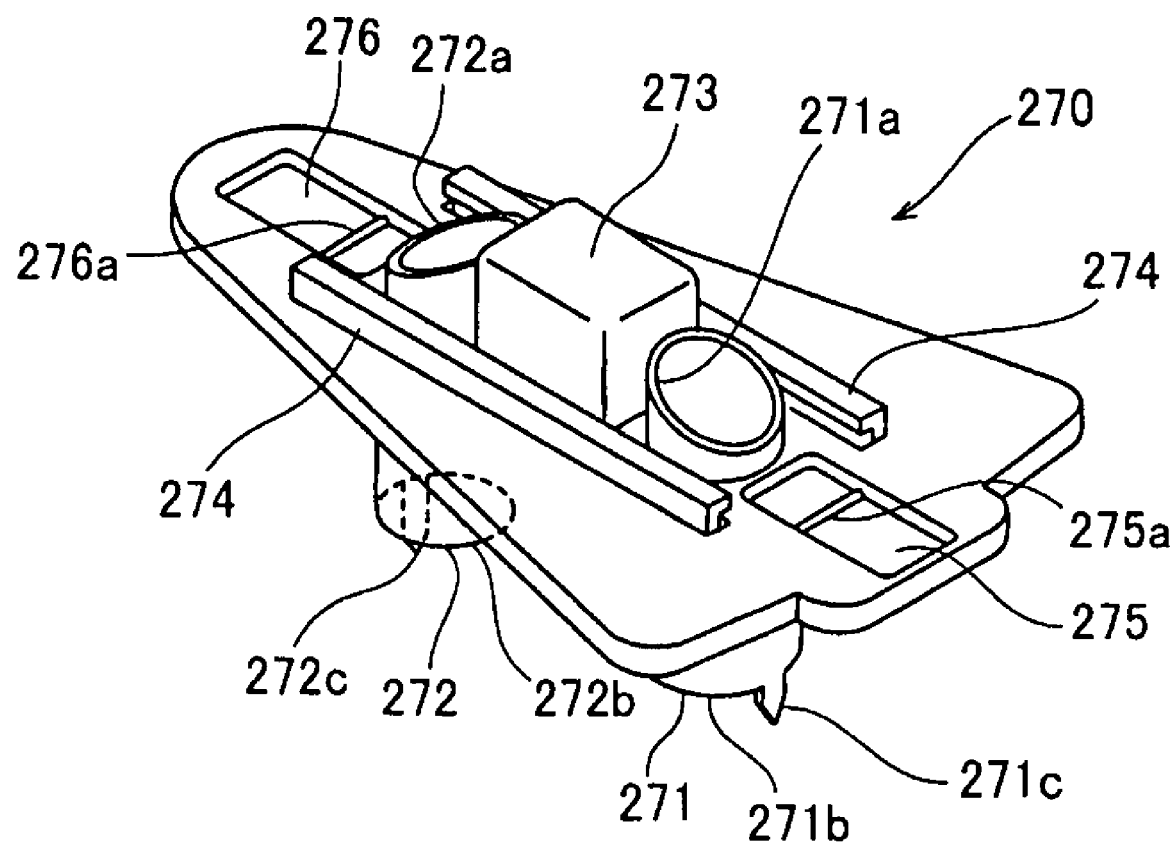
FIG. 28 is a perspective view showing an upper lid main body of the reagent-containing assembly according to the one embodiment.
Figure 29:
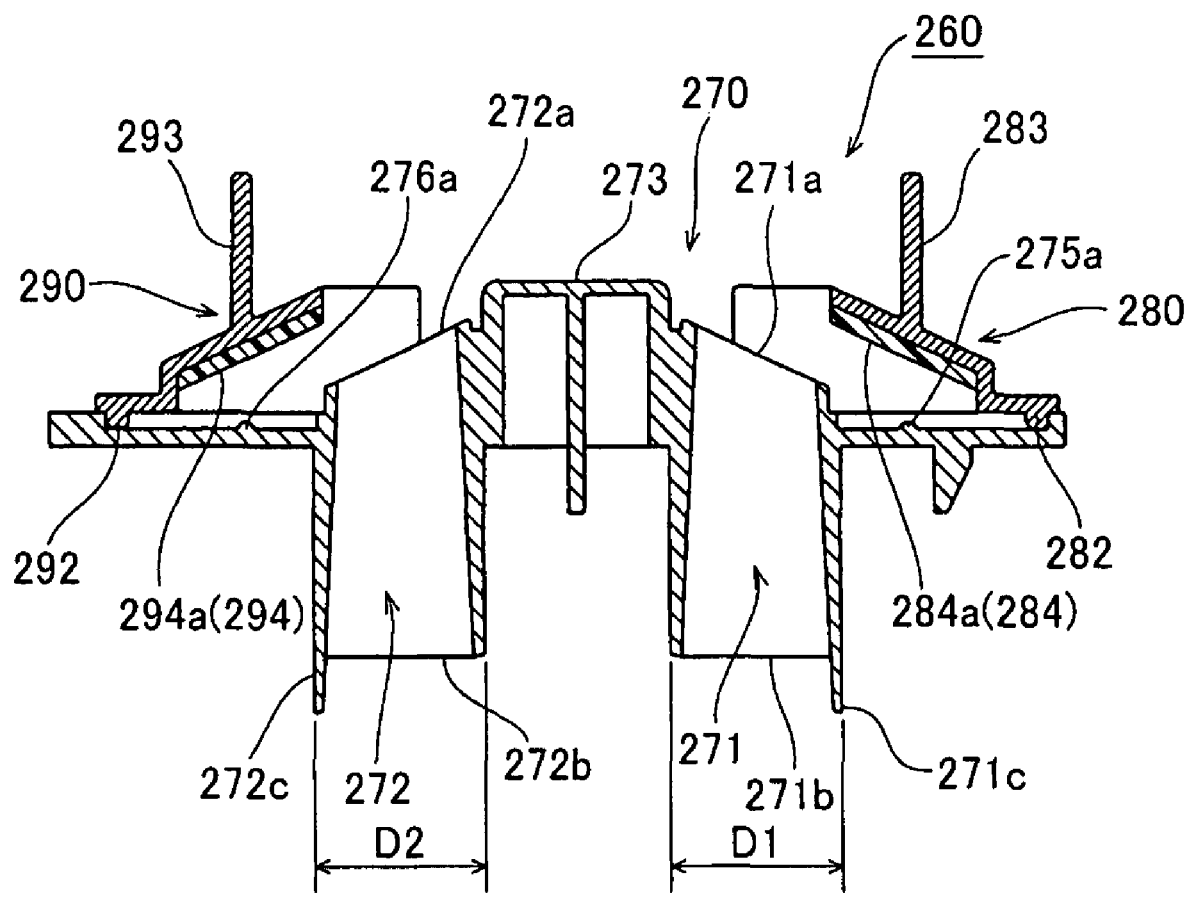
FIG. 29 is a cross sectional view showing the upper lid part of the reagent-containing assembly according to the one embodiment.

As shown in FIGS. 27 to 29, the upper lid part 260 includes an upper lid main body 270, and a slide lid 280 and a slide lid 290 slidably attached to the upper lid main body 270. The upper lid main body 270 has a tubular part 271 and a tubular part 272 to be inserted to the opening 212a of the reagent container 210 and the opening 222a of the reagent container 220, respectively, a reflection part 273 for reflecting the light irradiated by a reflection sensor 30f arranged on the lid 30, slide rails 274 for the slide lid 280 and the slide lid 290 to slide, and a concave part 275 and a concave part 276 for respectively regulating the position of the slide lid 280 and the slide lid 290.

As shown in FIGS. 28 and 29, the tubular part 271 is formed so that an opening end face 271a on the upper side has an inclined surface inclined by a predetermined angle from a horizontal plane. The opening end face 271b on the lower side is formed so as to be a horizontal plane. The pointed projecting portion 271c projecting downward is arranged on the opening end face 271b on the lower side. The aluminum seal 210a attached to the opening 212a of the reagent container 210 is broken by the projecting portion 271c. Similar to the tubular part 271, the tubular part 272 also includes an opening end face 272a on the upper side, an opening end face 272b on the lower side, and a pointed projecting portion 272c projecting downward from the opening end face 272b on the lower side.

Furthermore, the concave part 275 has a function of regulating the movement of the slide lid 280 by contacting the projecting part 282 of the slide lid 280 to be hereinafter described and suppressing the slide lid 280 from slipping off from the upper lid main body 270. A convex shaped rib 275a that engages the projecting part 282 of the slide lid 280 when the slide lid 280 is at a position of closing the opening end face 271a on the upper side of the tubular part 271 is arranged in the concave part 275. The slide lid 280 thus can be fixed with the slide lid 280 sealing the tubular part 282. Similar to the concave part 275, the concave part 276 is also arranged with a convex shaped rib 276a that engages the projecting part 282 of the slide lid 290 when the slide lid 290 is at a position of closing the opening end face 272a on the upper side of the tubular part 272.

The slide lid 280 is configured to open and close the tubular part 271 by sliding with respect to the upper lid main body 270. The slide lid 280 includes engagement parts 281 that engage with the slide rails 274, the projecting part 282 fitted into the concave part 275 of the upper lid main body 270, an engagement strip 283 that engages the openable/closable member 31 of the lid 30, and a contacting part 284 formed so as to have an inclined surface inclined by a predetermined angle. A plate shaped silicone sheet 284a that closely attaches to the opening end face 271a on the upper side of the tubular part when the slide lid 280 seals the tubular part is attached to the contacting part 284. Similar to the slide lid 280, the slide lid 290 is configured to open and close the tubular part 272 by sliding with respect to the upper lid main body 270. As shown in FIG. 29, the slide lid 290 includes engagement parts 291 (see FIG. 27) that engage with the slide rails 274, the projecting part 292, an engagement strip 293 that engages the openable/closable member 34 of the lid 30, and a contacting part 294 attached with a silicone sheet 294a.

Figure 30:
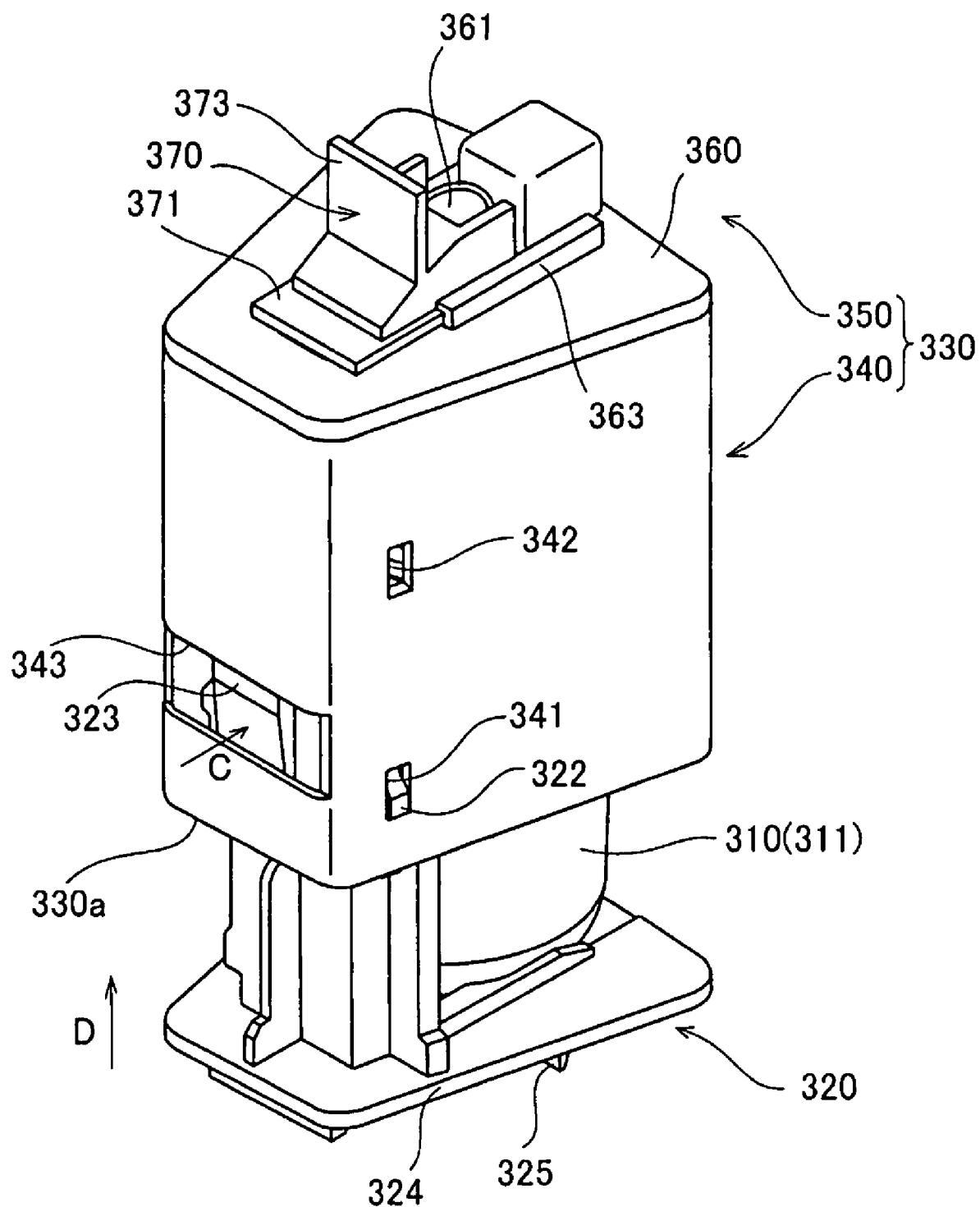
FIG. 30 is a perspective view showing an unused state of the reagent-containing assembly according to the one embodiment.
Figure 31:
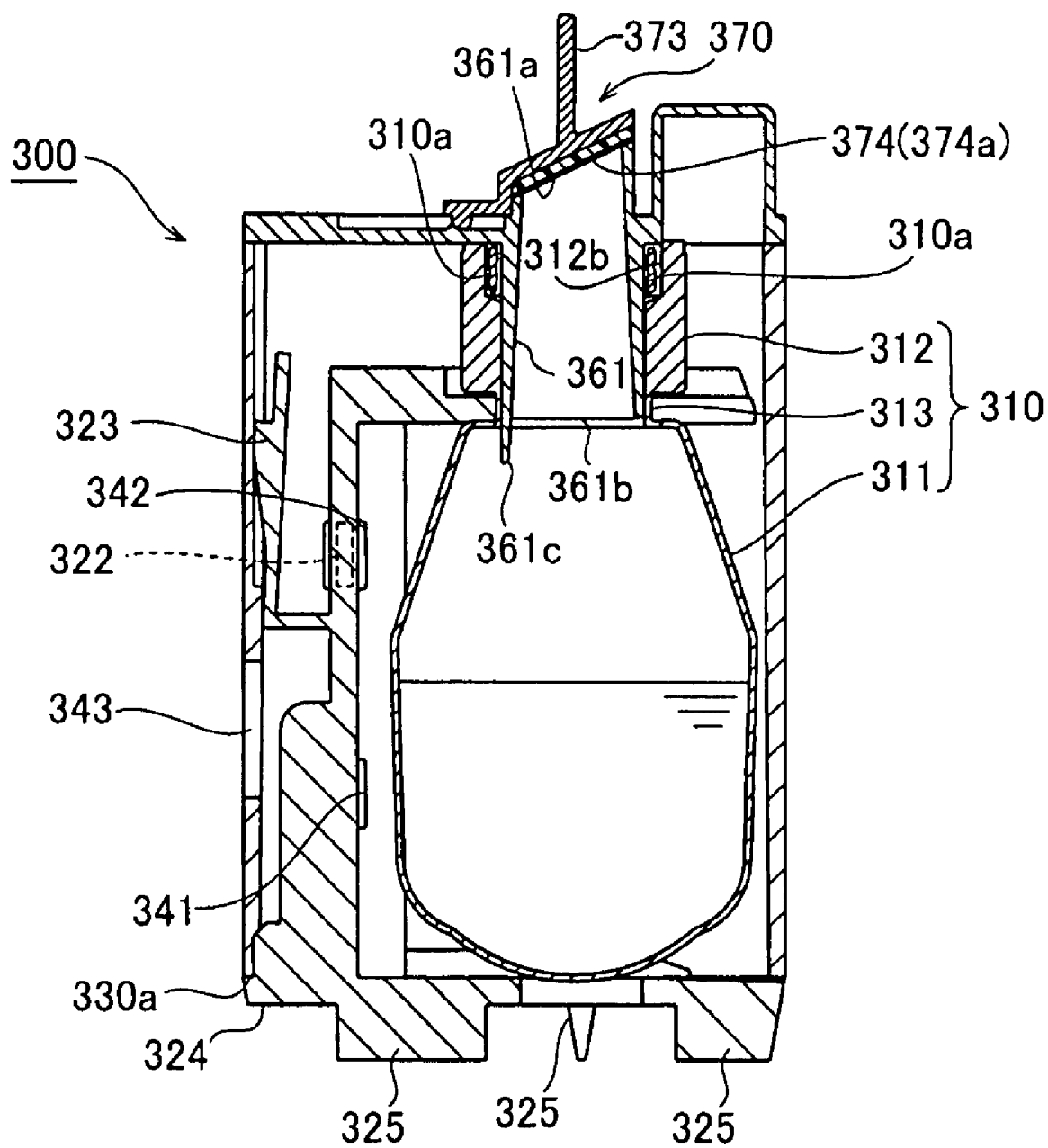
FIG. 31 is a cross sectional view showing an usage state of the reagent-containing assembly according to the one embodiment.

FIGS. 19 and 30 are cross sectional view and perspective view, respectively, showing an unused state of the reagent-containing assembly. FIG. 31 is a cross sectional view showing a usage state of the reagent-containing assembly. The method of using the reagent-containing assembly 300 according to the present embodiment will now be described with reference to FIGS. 19, 30, and 31.

The reagent-containing assembly 300 according to the present embodiment is supplied to the user in the state shown in FIGS. 19 and 30. In other words, when supplied to the user, the hole 343 of the case main body 340 and the engagement part 323 of the reagent container holder 320 are engaged, and the hole 341 of the case main body 340 and the hook 322 of the reagent container holder 320 are engaged. The reagent container holder 320 holding the reagent container 310 is thereby held at a predetermined position (hereinafter referred to as unused position) with respect to the case 330. In this state, the projecting portion 361c projecting from the opening end face 361b on the lower side of the tubular part 361 of the upper lid main body 360 and the aluminum seal 310a attached to the opening 312a of the reagent container 310 are spaced apart. Thus, the reagent container 310 has the opening 312a sealed by the aluminum seal 310a, and leakage and degradation of the reagent suppressed when supplied to the user.

When using the reagent-containing assembly 300, the user pushes the engagement part 323 of the reagent container holder 320 in the direction of the arrow C to release the engagement of the engagement part 323 of the reagent container holder 320 and the hole 343 of the case main body 340. The reagent container holder 320 thus can be moved upward with respect to the case 330. The reagent container holder 320 is moved upward (direction of arrow D) from the unused position with respect to the case 330. In the course of moving the reagent container holder upward with respect to the case 330, the aluminum seal 310a attached to the opening 312a of the reagent container 310 is broken by the projecting portion 361c projecting downward from the tubular part 361 of the upper lid main body 360. When the reagent container holder 320 is further moved upward, the tubular part 361 is inserted to the head part 312 of the reagent container 310. The pipette 9e of the reagent dispensing arm 9 thus can suction the reagent of the reagent container 310 through the tubular part 361 of the upper lid main body 360. In this case, the aluminum seal 310a broken by the projecting portion 361c is accommodated in the seal accommodating portion 312b arranged near the opening 312a of the reagent container 310. When the reagent container holder 320 is further moved upward, the hole 342 of the case main body 340 and the hook 322 of the reagent container holder 320 engage, and the bottom part 324 of the reagent container holder 320 and the lower end 330a of the case 330 contact, thereby closing the open end of the case 330. The reagent container holder 320 is thereby held at a position (usage position) at where the reagent-containing assembly 300 can be used for analysis with respect to the case 330, as shown in FIG. 31. Therefore, in the present embodiment, the reagent-containing assembly 300 can be used for analysis by positioning the reagent container holder 320 at the usage position with respect to the case 330 and opening the seal of the reagent container 310.

Figure 32:
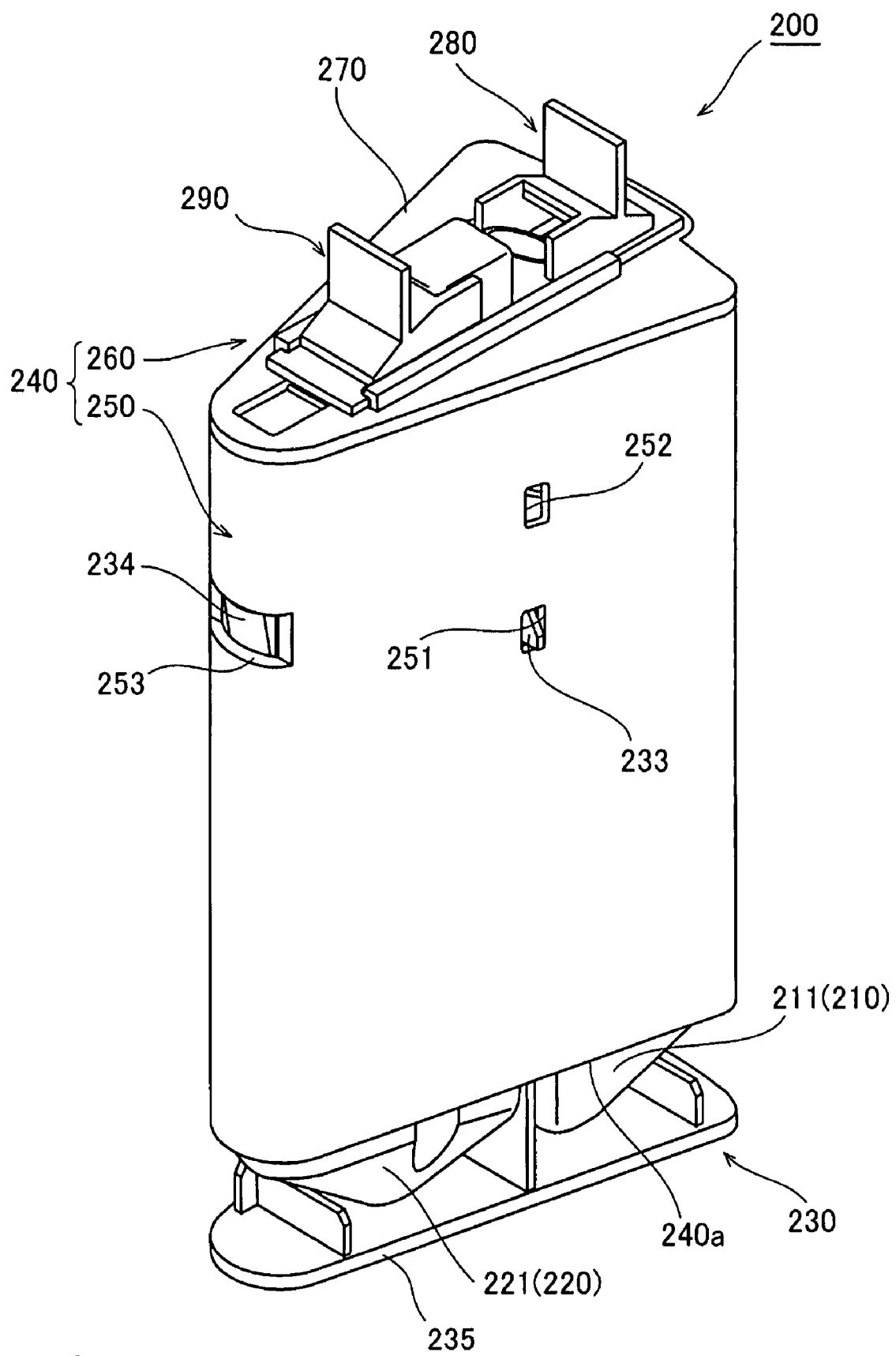
FIG. 32 is a perspective view showing an unused state of the reagent-containing assembly according to the one embodiment.
Figure 33:
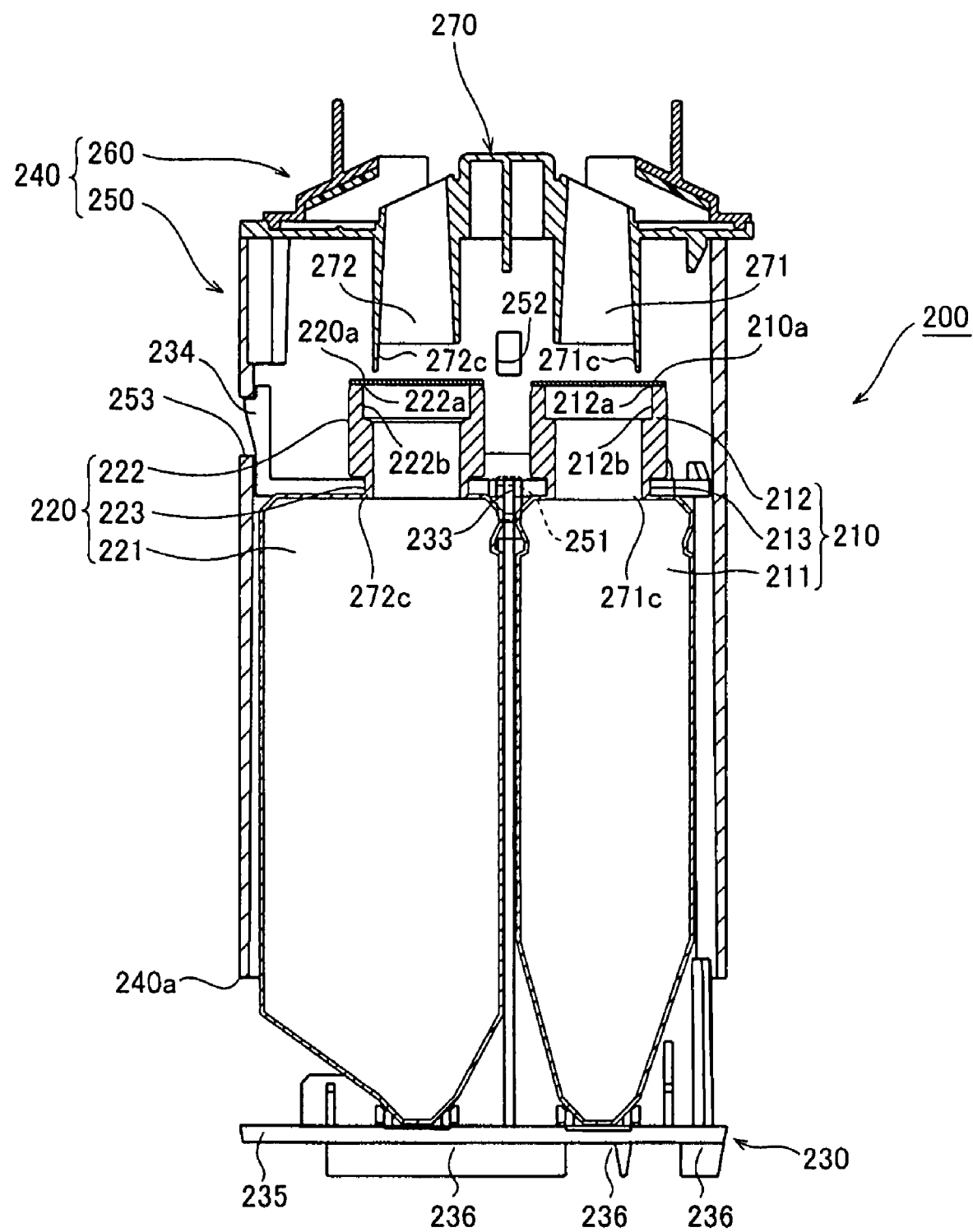
FIG. 33 is a cross sectional view showing the unused state of the reagent-containing assembly according to the one embodiment.
Figure 34:
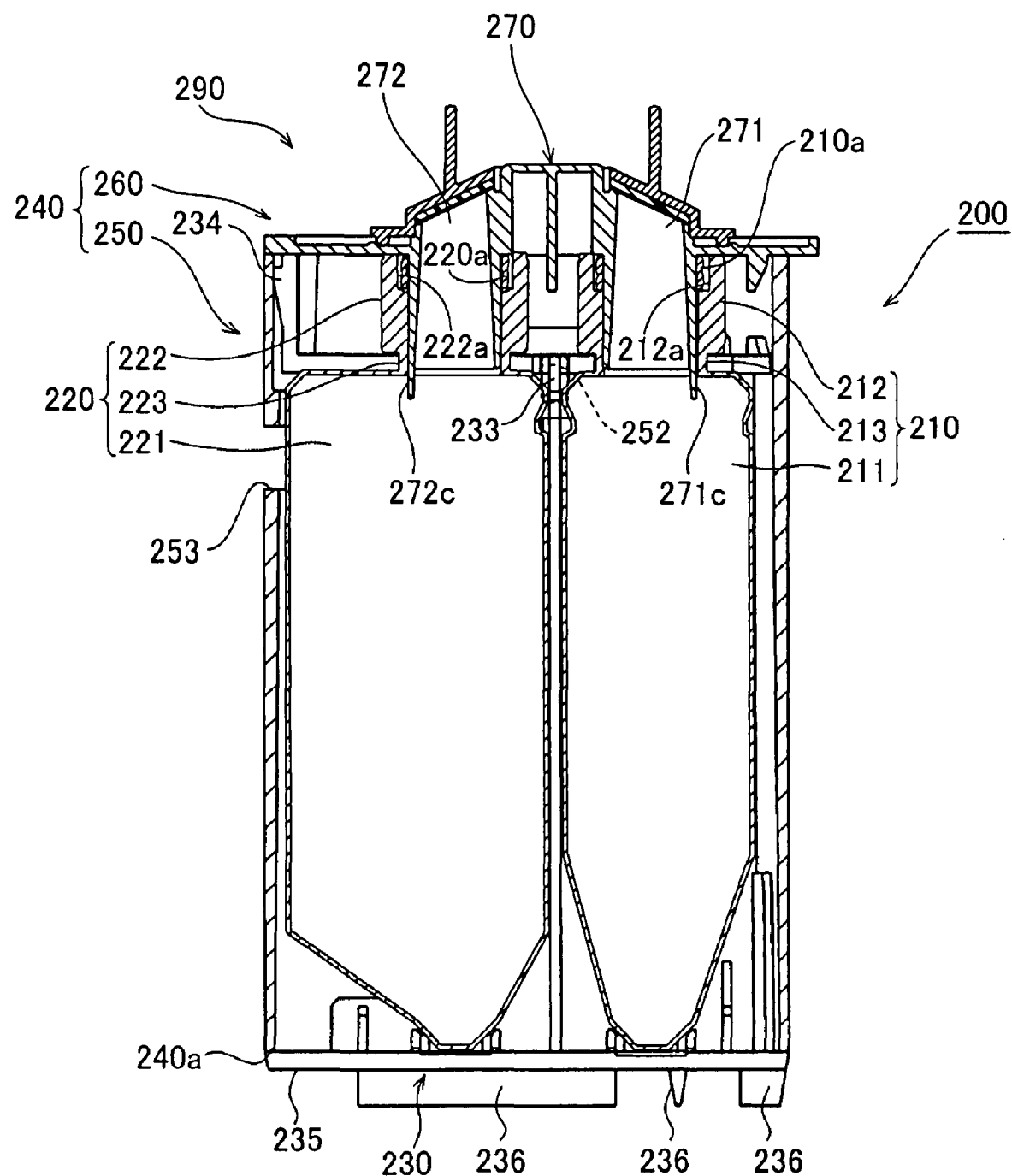
FIG. 34 is a cross sectional view showing the usage state of the reagent-containing assembly according to the one embodiment.

The reagent-containing assembly 200 can also be used for analysis with the seals of the reagent container 210 and the reagent container 220 broken through procedures similar to that of the reagent-containing assembly 300. FIGS. 32 and 33 are perspective view and cross sectional view, respectively, showing an unused state of the reagent-containing assembly. FIG. 34 is a cross sectional view showing a usage state of the reagent-containing assembly. The method of using the reagent-containing assembly 200 according to the present embodiment will now be described with reference to FIGS. 32 to 34.

The reagent-containing assembly 200 is supplied to the user in the state shown in FIGS. 32 and 33. In other words, it is held with respect to the case 240 at an unused position where the engagement part 234 of the reagent container holder 230 and the hole 253 of the case main body 250 engage, and the hook 233 of the reagent container holder 230 and the hole 251 of the case main body 250 engage. When the engagement of the engagement part 234 of the reagent container holder 230 and the hole 253 of the case main body 250 is released and the reagent container holder 230 is moved upward with respect to the case 240, the aluminum seal 210a and 220a attached to the opening 212a of the reagent container 210 and the opening 222a of the reagent container 220 are broken by the projecting portion 271c and the projecting portion 272c, respectively, of the upper lid main body 270. The broken aluminum seal 210a and 220a are accommodated in the seal accommodating portion 212b of the reagent container 210 and the seal accommodating portion (not shown) of the reagent container 220. When the reagent container holder 230 is further moved upward, the hook 233 of the reagent container holder 230 and the hole 252 of the case main body 250 engage, and the bottom part 235 of the reagent container holder 230 and the lower end 240a of the case 240 contact so that the lower end 240a of the case 240 closes, as shown in FIG. 34. The reagent container holder 230 is thereby held with respect to the case 240 at a position (usage position) at where the pipette 8e of the reagent dispensing arm 8 and the pipette 10e of the reagent dispensing arm 10 can suction the reagent of the reagent container 210 and the reagent container 220, respectively, through the tubular part 271 and the tubular part 272 of the upper lid main body 270.

Figure 35:
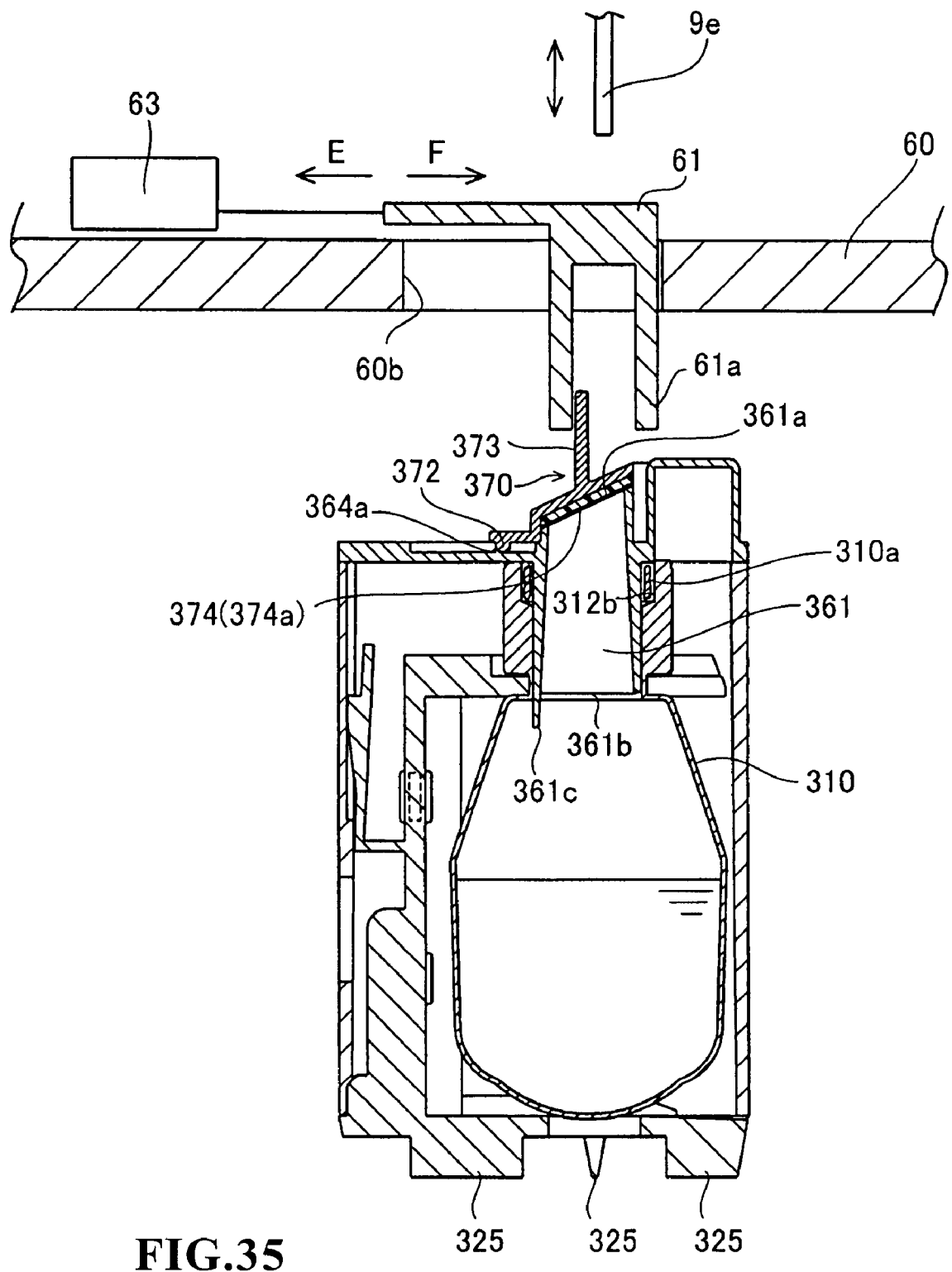
FIG. 35 is a cross sectional view showing a state in which a slide lid of the reagent-containing assembly is closed when suctioning reagent.
Figure 36:
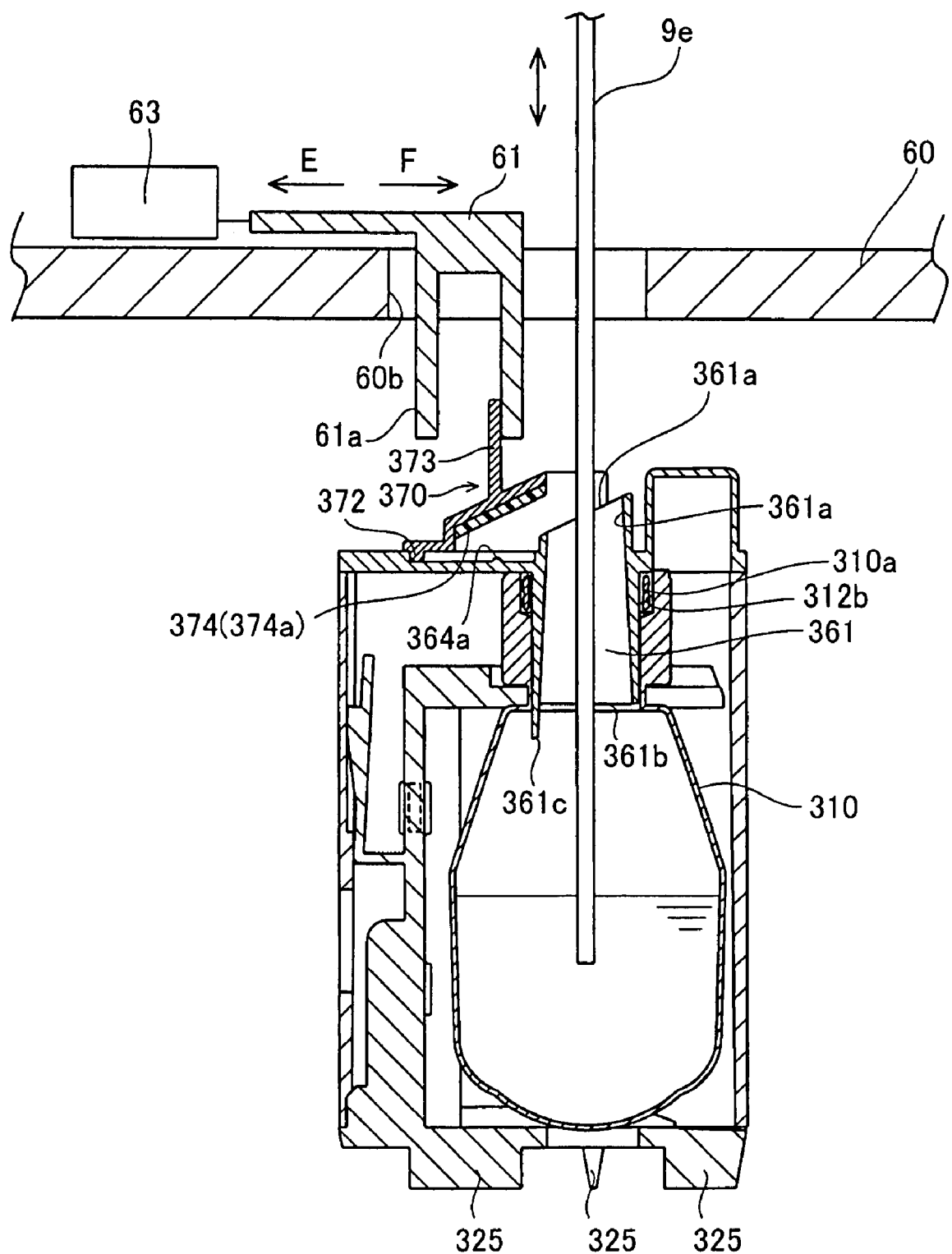
FIG. 36 is a cross sectional view showing a state in which the slide lid of the reagent-containing assembly is opened when suctioning reagent.

FIGS. 35 and 36 are cross sectional views showing the reagent-containing assembly, the hole of the lid, and the pipette for suctioning the reagent. The suctioning operation of suctioning the reagent from the reagent-containing assembly 300 according to the present embodiment with the pipette 9e of the reagent dispensing arm 9 will now be described with reference to FIGS. 1, 8, 11, 35, and 36.

First, the reagent-containing assembly 300 including the reagent container 310 accommodating the reagent to be suctioned is moved to below the hole 60b of the lid 60 by rotating the rack 600 holding the reagent-containing assembly 300 by the rotation shaft 52 (see FIG. 8) of the reagent holder 50. When the reagent-containing assembly 300 moves to below the hole 60b of the lid 60, the engagement strip 373 of the slide lid 370 is arranged between the two-forked engagement portions 61a of the openable/closable member 61 of the lid 60 if the slide lid 370 of the reagent-containing assembly 300 is closed, as shown in FIG. 35. When the reagent-containing assembly 300 moves to below the hole 60b of the lid 60, the engagement strip 373 of the slide lid 370 is guided by a guide strip 60g (see FIG. 11) arranged near the hole 60b of the lid 60 so as to be arranged between the two-forked engagement portions 61a of the openable/closable member 61 if the slide lid 370 of the reagent-containing assembly 300 is opened.

When the openable/closable member 61 is sled in the direction of the arrow E by the stepping motor 63 in this state, the engagement strip 373 of the slide lid 370 slides in the direction of arrow E with the two-forked engagement portions 61a and the slide lid 370 opens, as shown in FIG. 36. The pipette 9e of the reagent dispensing arm 9 can then be inserted inside the reagent container 310 through a region created when the openable/closable member 61 is sled of the holes 60b of the lid 60, and the tubular part 361. The pipette 9e is moved to above the hole 60b of the lid 60 by turning with the motor 9a and the drive transmitting portion 9b, the pipette 9e is lowered with the slide lid 370 opened so that the pipette 9e can be inserted into the reagent container 310 through the hole 60b and the tubular part 361, and the reagent is suctioned. The aluminum seal 310a that was sealing the reagent container 310 is accommodated in the seal accommodating portion 312b, and thus the broken aluminum seal 310a is suppressed from contacting the pipette 9e when the pipette 9e is inserted into the reagent container 310.

The pipette 9e that has suctioned the reagent is raised and turned by the motor 9a and the drive transmitting portion 9b to be moved to above the primary reaction unit 11 (see FIG. 1). The reagent suctioned from the reagent container 310 is then dispensed into the cuvette 150 of the primary reaction unit 11.

After the suction of the reagent is terminated, the turning member 61 is moved in the direction of the arrow F by the stepping motor 63, so that the engagement strip 373 of the slide lid 370 slides in the direction of the arrow F with the two-forked engagement portion 61a. The opening end face 361a on the upper side of the tubular part 361 and the silicone sheet 374a attached to the contacting part 374 of the slide lid 370 thereby closely attach, so that the reagent is in the sealed state. The projecting part 372 of the slide lid 370 and the rib 364a arranged in the concave part 364 of the upper lid main body 360 engage with the opening end face 361a on the upper side of the tubular part 361 and the silicone sheet 374a closely attached, and the slide lid 370 is fixed. The sealed state of the reagent is thereby maintained when the rack 600 is rotated and the reagent-containing assembly 300 is moved.

When suctioning the reagent from the reagent container 210 of the reagent-containing assembly 200 with the pipette 8a of the reagent dispensing arm 8, or when suctioning the reagent from the reagent container 220 of the reagent-containing assembly 200 with the pipette 10e of the reagent dispensing arm 10, the reagent is suctioned through the procedures similar to when suctioning from the reagent-containing assembly 300 with the pipette 9e of the reagent dispensing arm 9 described above.

In the present embodiment, the reagent in the reagent container 310 can be suctioned through the tubular part 361 and the opening 312a, the aluminum seal 310a of which is broken by the projecting portion 361c, when the reagent container holder 320 is held at the usage position with respect to the case 330, as described above. Since the user does not need to perform the task of peeling the aluminum seal 310a and the like, the reagent can be suctioned without contaminating the reagent accommodated in the reagent container 310, or while suppressing the occurrence of contamination accidents such as the reagent attaching to the user.

In the present embodiment, by arranging the seal accommodating portion 312b at where the aluminum seal 310a broken by the projecting portion 361c is to be accommodated in the reagent container 310, as described above, the reagent can be suctioned through the opening 312a and the tubular part 361 without being influenced by the broken aluminum seal 310a since the broken aluminum seal 310a is accommodated in the seal accommodating portion 312b so as not to be left on the path of the pipette 9e.

Furthermore, in the present embodiment, according to the configuration of holding the reagent container holder 320 with respect to the case 330 at the usage position at where the projecting portion 361c breaks the aluminum seal 310a and is positioned in the opening 312a of the reagent container 310 and an unused position at where the projecting portion 361c is spaced apart from the aluminum seal 310a, as described above, the reagent container holder 320 can be held at the unused position at where the projecting portion 361c is spaced apart from the aluminum seal 310a before using the reagent-containing assembly 300 and the reagent container holder 320 can be held at the usage position at where the projecting portion 361c breaks the aluminum seal 310a and is positioned in the opening 312a of the reagent container 310 when using the reagent-containing assembly 300. Thus, storage, conveyance, and the like of the reagent-containing assembly 300 can be performed with the reagent container holder 320 held at the unused position, and the reagent-containing assembly 300 can be used (suction reagent) with the reagent container holder 320 held at the usage position, thereby enhancing the convenience of the user.

In the present embodiment, the slide lid 370 capable of opening and closing the opening end face 361a on the upper side of the tubular part 361 is arranged on the upper lid part 350 of the case 330, as described above, whereby the opening end face 361a on the upper side of the tubular part 361 can be opened and closed by the slide lid 370 even after the aluminum seal 310a is broken by the projecting portion 361c. The slide lid 370 is opened and the reagent is suctioned when suctioning the reagent, and the slide lid 370 is closed and the reagent is stored in a sealed state when not using the reagent.

Furthermore, the slide lid 370 is sled to open and close the opening end face 361a on the upper side of the tubular part 361 in the present embodiment, as described above, whereby the opening end face 361a on the upper side of the tubular part 361 is easily opened and closed by sliding the slide lid 370.

Moreover, the silicone sheet 375 for sealing the opening end face 361a on the upper side of the tubular part 361 is attached to the slide lid 370 in the present embodiment, as described above, whereby the sealed state of the reagent is easily obtained by closing the slide lid 370 and closely attaching the silicone sheet 375 to the opening end face 361a on the upper side of the tubular part 361.

In the present embodiment, the convex portions 211a and 211b projecting towards the inner side and extending in the vertical direction and in the horizontal direction are arranged in the reagent container 210, as described above, whereby the movement of the reagent is suppressed as the reagent contacts the convex portions 211a and 211b arranged on the inner surface side of the reagent container 210 when the reagent moves in the reagent container 210 with the rotation and movement of the reagent-containing assembly 200 in the reagent holder 20. The reagent is thereby suppressed from foaming.

In the present embodiment, when the aluminum seal 310a is broken by the projecting portion 361c and opened, the tubular part 361 is fitted to the opening 312a, and the pipette 9e for suctioning the reagent is inserted into the reagent container 310 through the tubular part 361, as described above, whereby the pipette 9e can be easily inserted into the reagent container 310 through the tubular part 361 fitted to the opening 312a after the aluminum seal 310a is broken by the projecting portion 361c.

According to the configuration in which the lower end 330a of the case 330 is closed by the bottom part 324 of the reagent container holder 320 when the aluminum seal 310a is broken and opened by the projecting portion 361c in the present embodiment, as described above, the case 330 and the reagent container holder 320 are integrated with the aluminum seal 310a broken by the projecting portion 361c and opened, and thus the reagent-containing assembly 300 can be readily handled.

In the present embodiment, the slit 344 that enables the reagent in the reagent container 310 to be viewed is formed in the case main body 340 of the box shaped case 330, as described above, and thus the user can check the amount of reagent in the reagent container 310 through the slit 344.

In the present embodiment, the rib 435 for engaging the groove 71a of the mounting part 71 of the raising and lowering unit 70 is arranged on the bottom part 324 of the reagent container holder 320, as described above, whereby the reagent-containing assembly 300 is easily raised and lowered by the raising and lowering unit 70 by engaging the rib 325 to the groove 71a.

The embodiments disclosed herein are illustrative and should not be construed as being restrictive. The scope of the invention is defined by the appended claims rather than by the description of the embodiments, and all changes that fall within meets and bounds of the claims, or equivalence of such meets and bounds are therefore intended to be embraced by the claims.

For instance, an example of using the reagent-containing assemblies 200 and 300 in the immune analyzer 1 has been described in the embodiment, but the present invention is not limited thereto, and such reagent-containing assemblies may be used in other analyzers as long as reagent is used in the analyzer.

An example of configuring the reagent-containing assembly 200 so as to hold two reagent containers 210 and 220, and configuring the reagent-containing assembly 300 so as to hold one reagent container 310 has been described in the above embodiments, but the present invention is not limited thereto, and the reagent-containing assembly may be configured to hold three or more reagent containers.

Figure 37:
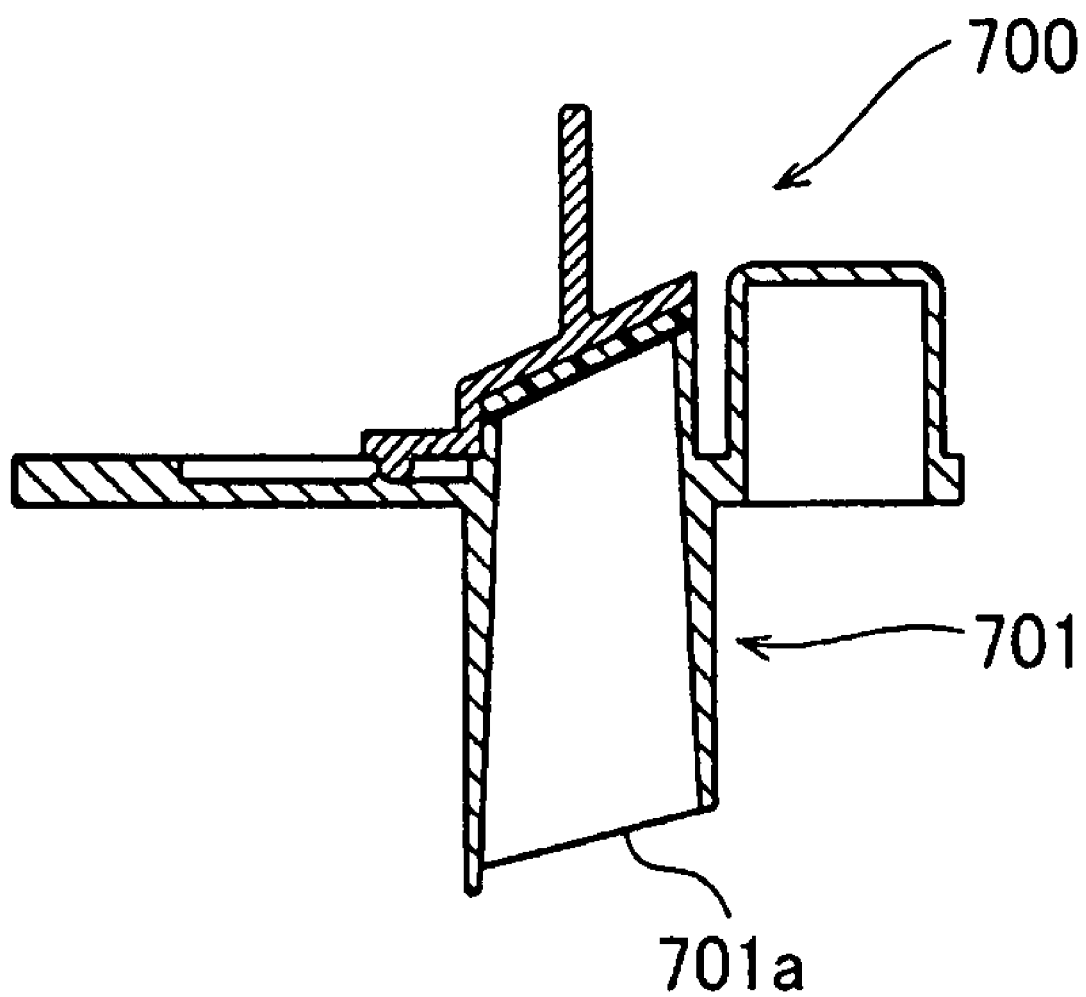
FIG. 37 is a cross sectional view showing a variant of the upper lid main body of the reagent-containing assembly according to the one embodiment.

An example of forming a cut-out of the opening end face 361b on the lower side of the tubular part 361 of the upper lid main body 360 so as to be a horizontal plane has been described in the above embodiment, but the present invention is not limited thereto, and the cut-out of an opening end face 701a on the lower side of a tubular part 701 may be formed to an inclined surface inclined by a predetermined angle as in an upper lid main body 700 according to a variant shown in FIG. 37.

What is claimed is:

1. An assembly for containing reagent, the assembly comprising:
   a reagent-accommodating section comprising an opening sealed by a seal member; and
   a seal-opening section comprising:
   an access part comprising a suction hole;

a breaking portion projecting from the access part for breaking the seal member; and a lid part operable in combination with a linear slide rail part to cover and uncover the suction hole by sliding along the linear slide rail part, wherein the suction hole is configured to provide access to the reagent-accommodating section when the seal member has been broken by the breaking portion, and wherein the reagent-accommodating section and the seal-opening section are configured for detachable engagement with each other.

2. The assembly according to claim 1, wherein the reagent-accommodating section and the seal-opening section are further configured for detachable engagement at a plurality of engagement positions.

3. The assembly according to claim 2, the plurality of engagement positions comprises a first position in which the seal member remains intact and a second position in which the seal member is broken.

4. The assembly according to claim 1, wherein the lid part comprises a sheet member made up of elastic body for sealing the suction hole.

5. The assembly according to claim 1, wherein the reagent-accommodating section comprises a reagent container and a reagent container holder configured for detachably holding the reagent container.

6. The assembly according to claim 5, wherein the reagent container comprises a convex part arranged projecting towards the inner side of the reagent container and extending in at least one of up and down direction and horizontal direction.

7. The assembly according to claim 5, wherein the reagent container comprises an engagement part configured for engaging the reagent container with the reagent container holder; and the reagent container holder is configured to hold the reagent container by engaging the engagement part of the reagent container.

8. The assembly according to claim 1, wherein
the access part comprises a tubular part comprising the suction hole;
the breaking portion is arranged at a lower part of the tubular part; and
the seal opening section is configured so that the tubular part is inserted into the opening when the seal member is broken by the breaking portion.

9. The assembly according to claim 1, wherein
the seal-opening section comprises a box shape having an open end for accommodating the reagent-accommodating section;
the reagent-accommodating section comprises a closing part for closing the open end of the seal-opening section; and
the seal-opening section and the reagent-accommodating section are configured so that the open end is closed by the closing part after the seal member is broken by the breaking portion.

10. The assembly according to claim 1, wherein
the seal-opening section comprises a box shape having an open end for accommodating the reagent-accommodating section; and the seal-opening section comprises a slit through which reagent in the reagent-accommodating section can be viewed.

11. The assembly according to claim 5, wherein a bottom part of the reagent container holder comprises an engagement part for engaging an exterior conveyance device.

12. The assembly according to claim 1, wherein
the access part comprises a tubular part comprising the suction hole;
the opening has a circular form; and
the tubular part has an outer diameter smaller than a diameter of the opening.

13. The assembly according to claim 5, further comprising reagent contained in the reagent container.

14. The assembly according to claim 13, wherein the reagent is reagent used in immune measurement.

15. An assembly for containing reagent, the assembly comprising:
a reagent container comprising an opening sealed by a seal member;
a holder configured for holding the reagent container; and
a case, movable in a direction towards a bottom part of the holder, configured for covering the reagent container; wherein
the case comprises:
an access part comprising a suction hole;
a breaking portion projecting from the access part for breaking the seal member; and
a lid part operable in combination with a linear slide rail part to cover and uncover the suction hole by sliding along the linear slide rail part,
wherein the suction hole is configured to provide access to the reagent container when the seal member has been broken by the breaking portion, and
the holder and case are configured for detachable engagement with each other.

16. The assembly according to claim 15, further comprising reagent contained in the reagent container.

17. The assembly according to claim 15, wherein the reagent container and the holder are integrally formed.

18. An assembly for containing reagent, the assembly comprising:
a holder for holding a reagent container comprising an opening sealed by a seal member; and
a case, movable in a direction towards a bottom part of the holder, configured for covering the reagent container; wherein
the case comprises:
an access part comprising a suction hole;
a breaking portion projecting from the access part for breaking the seal member; and
a lid part operable in combination with a linear slide rail part to cover and uncover the suction hole by sliding along the linear slide rail part,
wherein the suction hole is configured to provide access to the reagent container when the seal member has been broken by the breaking portion, and
the holder and case are configured for detachable engagement with each other.

* * * * *